United States Patent

Kitsuki et al.

[11] Patent Number: 5,714,457
[45] Date of Patent: Feb. 3, 1998

[54] 2-HYDROXYPROPANEDIAMINE DERIVATIVE AND DETERGENT COMPOSITION CONTAINING THE SAME

[75] Inventors: Tomohito Kitsuki, Naga-gun; Mitsuru Uno, Wakayama; Katsumi Kita, Izumisano; Yoshiaki Fujikura, Utsunomiya; Akiko Nakano, Higashiosaka; Masaki Tosaka, Kishiwada; Kazuyuki Yahagi, Tokyo; Shigeru Tamura, Kainan; Kazunari Maruta, Wakayama, all of Japan

[73] Assignee: Kao Corporation, Tokyo, Japan

[21] Appl. No.: 569,128

[22] PCT Filed: Jul. 11, 1994

[86] PCT No.: PCT/JP94/01129

§ 371 Date: Jan. 11, 1996

§ 102(e) Date: Jan. 11, 1996

[87] PCT Pub. No.: WO95/01955

PCT Pub. Date: Jan. 19, 1995

[30] Foreign Application Priority Data

| Jul. 9, 1993 | [JP] | Japan | 5-170447 |
| Jul. 9, 1993 | [JP] | Japan | 5-170448 |
| Dec. 28, 1993 | [JP] | Japan | 5-335780 |
| Dec. 28, 1993 | [JP] | Japan | 5-335788 |
| Dec. 28, 1993 | [JP] | Japan | 5-335789 |

[51] Int. Cl.$^6$ ............................. C11D 1/02
[52] U.S. Cl. ............... 510/499; 510/119; 510/130; 510/477; 510/490; 558/25; 560/196; 562/102; 562/564
[58] Field of Search ........... 510/499, 119, 510/130; 562/102, 564; 558/25; 560/196

[56] References Cited

U.S. PATENT DOCUMENTS

| 3,689,544 | 9/1972 | Scanlon et al. | 562/564 |
| 3,780,099 | 12/1973 | Scanlon et al. | 562/564 |
| 4,533,479 | 8/1985 | Cargnino et al. | 562/564 |
| 5,099,065 | 3/1992 | Kubo et al. | 562/564 |

*Primary Examiner*—Prince Willis, Jr.
*Assistant Examiner*—Cephia D. Toomer
*Attorney, Agent, or Firm*—Oblon, Spivak, McClelland, Maier & Neustadt, P.C.

[57] ABSTRACT

The present invention relates to a 2-hydroxypropanediamine derivative represented by the following general formula (1):

$$R^1-\underset{\underset{\underset{Y^1}{X}}{(CO)_n}}{N}-CH_2CHCH_2-\underset{Y^2}{N}-\underset{\underset{\underset{Y^1}{X}}{(CO)_n}}{R^2} \qquad (1)$$

wherein $R^1$ and $R^2$ mean individually a linear or branched $C_6$–$C_{36}$ alkyl or alkenyl group. X denotes a $C_1$–$C_6$ alkylene or alkenylene group which may be substituted by at least one hydroxyl, sulfonic or carboxyl group and has 1–6 carbon atoms, $y^1$ is a sulfonic group, a sulfuric acid residue or a carboxyl group, $y^2$ means a hydroxyl group, a sulfuric acid residue or $$-\text{OCX}-\text{COOH},\overset{\underset{\parallel}{O}}{}$$

and n stands for 0 or 1, or a salt or quaternized product thereof, and a detergent composition containing such a compound. This compound is low in irritativeness to the skin and hair and excellent in foamability, and can give a pleasant feeling to the user's skin and the like.

15 Claims, 5 Drawing Sheets

2-HYDROXYPROPANEDIAMINE DERIVATIVE AND DETERGENT COMPOSITION CONTAINING THE SAME

TECHNICAL FIELD

The present invention relates to a 2-hydroxypropanediamine derivative, or a salt or quaternized product thereof, which is useful as a base for hair and skin cosmetic compositions, a detergent, an emulsifying agent, a conditioning agent, or the like.

BACKGROUND ART

Surfactants such as alkylsulfates, polyoxyethylene alkylsulfates and alkylbenzenesulfonates have heretofore been used as detergents. However, many of these surfactants involve a problem that they irritate the skin to a somewhat strong extent upon their use. For this reason, surfactants low in skin irritation, such as alkylphosphates and salts of acylated amino acids, have come to be used as bases for hair and skin cosmetic compositions, emulsifying agents or detergents for the skin and the like. With the diversification of consumer demand and inclination to high-quality goods, there have recently been demand for development of compounds which have good foamability and such effects that a pleasant feeling can be given to the user's skin and the like, in addition to low irritativeness to the skin and the like. However, no compound fully satisfying these requirements has been yet developed.

Accordingly, it is an object of the present invention to provide a compound which can solve the above problems, has low irritativeness to the skin and the like and excellent foamability, can give a pleasant feeling to the user's skin and the like, and is useful as a base for hair and skin cosmetic compositions, a detergent, an emulsifying agent, a conditioning agent, or the like.

DISCLOSURE OF THE INVENTION

In view of the foregoing circumstances, the present inventors have carried out an extensive investigation. As a result, it has been found that a novel compound represented by the general formula (1), which will be described subsequently, has low irritativeness to the skin and the like, gives a pleasant feeling to the user's skin and the like, and has excellent foamability, and that the incorporation of this compound permits the provision of a detergent excellent in detergency and foaming power, and free from irritation to the skin and the like, thus leading to completion of the present invention.

According to the present invention, there is thus provided a 2-hydroxypropanediamine derivative represented by the following general formula (1):

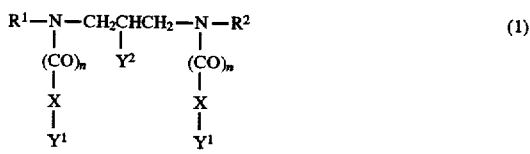

wherein $R^1$ and $R^2$ are identical with or different from each other and mean individually a linear or branched alkyl or alkenyl group having 6–36 carbon atoms, X denotes an alkylene or alkenylene group which may be substituted by at least one hydroxyl, sulfonic or carboxyl group and has 1–6 carbon atoms, $Y^1$ is a sulfonic group, a sulfuric acid residue or a carboxyl group, $Y^2$ means a hydroxyl group, a sulfuric acid residue or

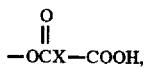

and n stands for 0 or 1, or a salt or quaternized product thereof.

According to the present invention, there is also provided a detergent composition comprising this 2-hydroxypropanediamine derivative (1), or a salt or quaternized product thereof.

BEST MODE FOR CARRYING OUT THE INVENTION

Figure 1:
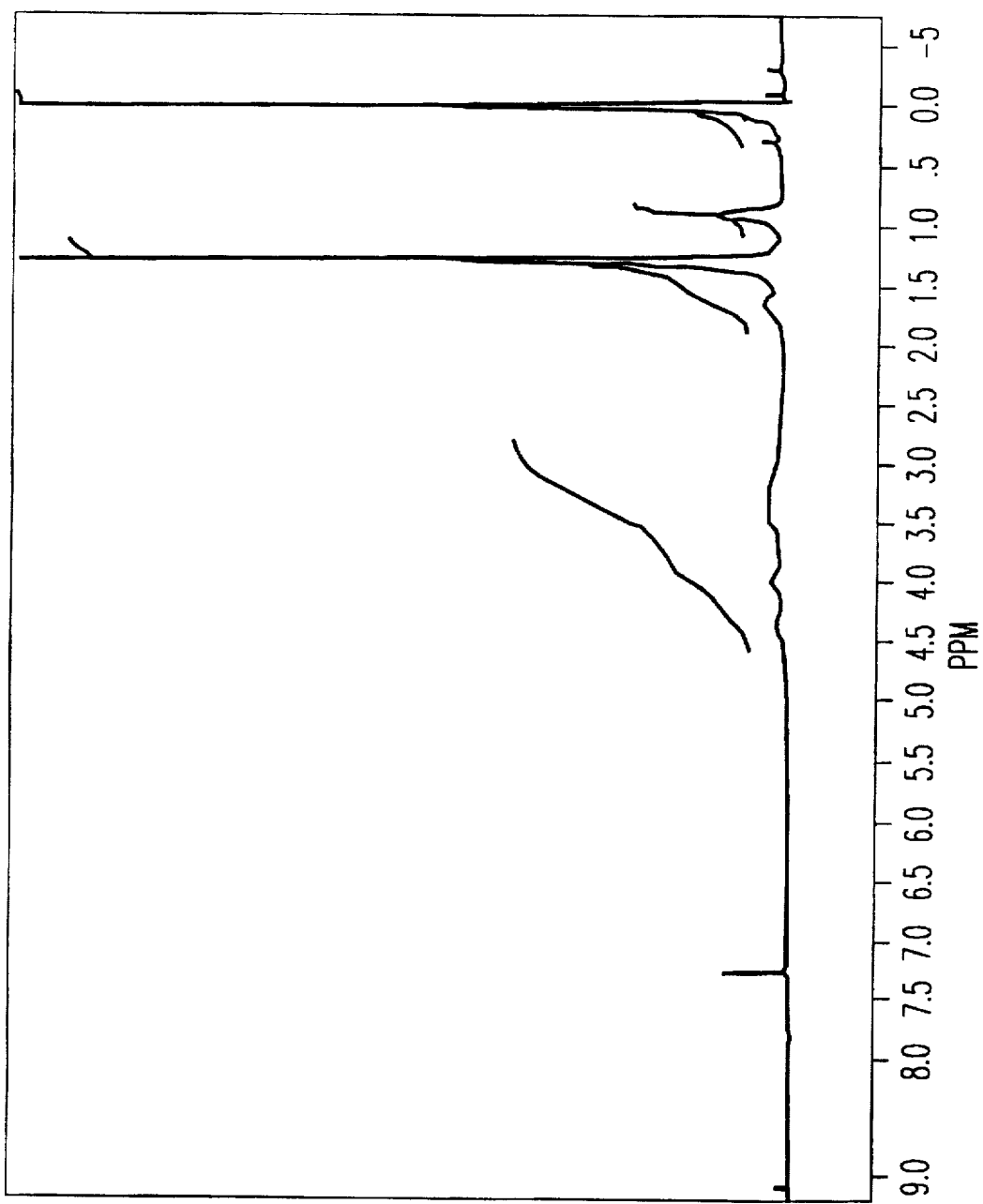
FIG. 1 illustrates an $^1$H-NMR chart of a compound obtained in Example 5.

As compounds having a 2-hydroxypropanediamine structure, there have been known those disclosed in U.S. Pat. No. 3,654,158, DE Patent No. 3,607,884, U.S. Pat. No. 4,982,000 and Japanese Patent Application Laid-Open Nos. 233264/1989 and 223515/1990, and the like. However, these compounds have no anionic functional groups such as a carboxyl group, a sulfonic group and a sulfuric acid residue, and are hence greatly different from the compounds according to the present invention in both structure and function.

In the formula (1), examples of the linear or branched alkyl groups having 6–36 carbon atoms and indicated by $R^1$ and $R^2$ include linear alkyl groups such as hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl groups, and branched alkyl groups corresponding to these linear groups. On the other hand, examples of the linear or branched alkenyl groups having 6–36 carbon atoms include linear alkenyl groups such as hexenyl, heptenyl, octenyl, nonenyl, decenyl, dodecenyl, undecenyl, tridecenyl, tetradecenyl, pentadecenyl, hexadecenyl, heptadecenyl, octadecenyl, nonadecenyl, eicosenyl, heneicosenyl, docosenyl, tricosenyl and tetracosenyl groups, and branched alkenyl groups corresponding to these linear groups. Among these, alkyl or alkenyl groups having 6–24 carbon atoms, particularly, alkyl groups having 6–24 carbon atoms, more particularly, alkyl groups having 6–18 carbon atoms are preferred as $R^1$ and $R^2$.

In the formula (1), examples of the alkylene or alkenylene groups having 1–6 carbon atoms and indicated by X and $X^1$, include methylene, ethylene, trimethylene, tetramethylene, pentamethylene, hexamethylene, methylethylene, ethylethylene, ethenylene, propenylene, butenylene, pentenylene and hexenylene. Of these, those having 1–4 carbon atoms are preferred and those having 1–3 carbon atoms are more preferred, with methylene, ethylene, trimethylene and ethenylene group being particularly preferred.

These alkylene or alkenylene groups may be substituted by at least one hydroxyl group (—OH), sulfonic group (—SO$_3$H) or carboxyl group (—COOH), with the proviso that $X^1$ may be substituted by at least one hydroxyl or carboxyl group). These substituent groups may be replaced either singly or in any combination of 2 to 4 groups.

Examples of the hydroxyl-substituted alkylene or alkenylene groups include 1-hydroxyethylene, 2-hydroxyethylene, 1,2-dihydroxyethylene, 1-hydroxytrimethylene, 2-hydroxytrimethylene 3-hydroxytrimethylene, 1,2-dihydroxytrimethylene, 1,3-dihydroxytrimethylene, 1,2,3-trihydroxytrimethylene, 1-hydroxytetramethylene, 2-hydroxytetramethylene, 3-hydroxytetramethylene, 4-hydroxytetramethylene, 1,2-dihydroxytetramethylene, 1,3-dihydroxytetramethylene, 1,4-dihydroxytetramethylene, 2,3-dihydroxytetramethylene, 2,4-dihydroxytetramethylene, 3,4-dihydroxytetramethylene, 1,2,3-trihydroxytetramethylene, 2,3,4-trihydroxytetramethylene, 1,3,4-trihydroxytetramethylene and 1,2,3,4-tetrahydroxytetramethylene groups. Of these, 1,2-dihydroxyethylene, 2-hydroxyethylene and 2-hydroxytrimethylene groups are particularly preferred.

Examples of the sulfonic group-substituted alkylene or alkenylene groups include 1-sulfoethylene, 2-sulfoethylene, 1-sulfotrimethylene, 2-sulfotrimethylene, 3-sulfotrimethylene, 1-sulfotetramethylene, 2-sulfotetramethylene, 3-sulfotetramethylene, 4-sulfotetramethylene, 1,3-disulfotetramethylene, 1,4-disulfotetramethylene, 2,3-disulfotetramethylene and 2,4-disulfotetramethylene groups. Of these, 1-sulfoethylene and 2-sulfoethylene groups are particularly preferred.

Examples of the carboxyl group-substituted alkylene or alkenylene groups include 1-carboxyethylene, 2-carboxyethylene, 1-carboxytrimethylene, 2-carboxytrimethylene, 3-carboxytrimethylene and 1-carboxytetramethylene groups.

Examples of the alkylene or alkenylene groups substituted by hydroxyl and carboxyl groups include 2-carboxy-1-hydroxytrimethylene, 2-carboxy-1,3-dihydroxytrimethylene, 2-carboxy-2-hydroxytrimethylene and 3-carboxy-2,4-dihydroxytetramethylene groups. Of these, 2-carboxy-2-hydroxytrimethylene group is preferred.

Examples of the alkylene or alkenylene groups substituted by hydroxyl and sulfonic groups include 1-hydroxy-2-sulfoethylene, 2-hydroxy-1-sulfoethylene, 1-hydroxy-2-sulfotrimethylene, 1-hydroxy-3-sulfotrimethylene, 2-hydroxy-1-sulfotrimethylene, 2-hydroxy-3-sulfotrimethylene, 1,2-dihydroxy-3-sulfotrimethylene, 1,3-dihydroxy-2-sulfotrimethylene, 1-hydroxy-2-sulfotetramethylene, 1-hydroxy-4-sulfotetramethylene, 2-hydroxy-4-sulfotetramethylene and 3-hydroxy-4-sulfotetramethylene groups.

Since the compounds (1) according to the present invention have at least one sulfonic group (—SO$_3$H), sulfuric acid residue (—OSO$_3$H) or carboxyl group (—COOH), they can form salts with various basic substances. Examples of such salts include alkali metal salts, alkaline earth metal salts, amine salts, basic amino acid salts and ammonium salts. Specific examples thereof include salts with sodium, potassium, lithium, magnesium, calcium, trimethylamine, triethylamine, tributylamine, monoethanolamine, diethanolamine, triethanolamine, lysine, arginine, choline and ammonia. Of these, alkali metal salts, particularly, the sodium salts are preferred. Incidentally, since the compounds (1) according to the present invention have tertiary amino groups, they may have a quaternary salt structure that a proton is coordinated on the nitrogen atom of the tertiary amino group, and so the tertiary amino group turns into an ammonium cation, and the sulfonic group, sulfuric acid residue or carboxyl group becomes a sulfonate, sulfate or carboxylate anion.

The compound (1) according to the present invention may be quaternized as needed. Specific examples thereof include compounds (1f) in which two nitrogen atoms in the formula (1) are quaternized.

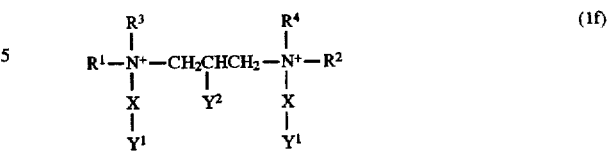

wherein $R^3$ and $R^4$ mean individually an alkyl or alkenyl group which may be substituted by at least one sulfonic, carboxyl or hydroxyl group and has 1–6 carbon atoms, a benzyl group, or —(R$^5$O)$_m$H in which R$^5$ denotes an alkylene group having 2–4 carbon atoms, and m stands for a number of 1–50. Here, examples of the alkyl group which may be substituted by at least one sulfonic, carboxyl or hydroxyl group and has 1–6 carbon atoms include methyl, ethyl, propyl, isopropyl, butyl, pentyl, hexyl, hydroxyethyl, 1,2-dihydroxypropyl, carboxymethyl and 2-hydroxy-3-sulfopropyl groups. Specific examples of the group represented by the radical —(R$^5$O)$_m$H include polyoxyethylene and polyoxypropylene groups. Of these groups, those in which m is 1–20 are preferred. The quaternized products of the compounds (1) according to the present invention may exist where n in the formula (1) is 0.

The compounds (1) according to the present invention are prepared in accordance with, for example, any one of the following reaction schemes a to d:

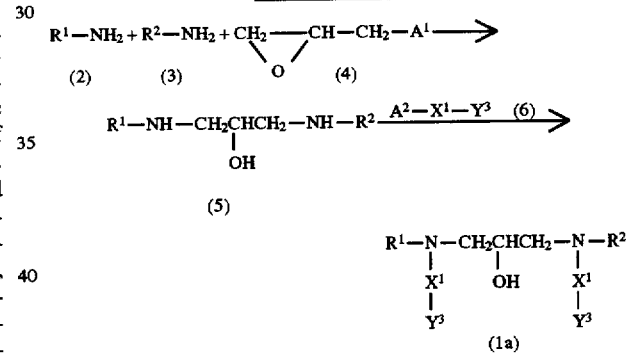

wherein $A^1$ and $A^2$ mean individually a halogen atom, $X^1$ denotes an alkylene or alkenylene group which may be substituted by at least one hydroxyl or carboxyl group and has 1–6 carbon atoms, $Y^3$ stands for a sulfonic or carboxyl group, and $R^1$ and $R^2$ have the same meaning as defined above.

More specifically, a compound (1a) according to the present invention is prepared by reacting two amines ((2) and (3)) with an epihalohydrin (4) and then reacting the resulting amine derivative (5) with a compound (6) or a salt thereof.

The reaction of the two amine with the epihalohydrin may be conducted in accordance with, for example, U.S. Pat. No. 3,017,258 or U.S. Pat. No. 3,654,158.

The reaction of the amine derivative (5) with the compound (6) or the salt thereof is conducted, for example, by reacting the amine derivative (5) with the compound (6) or the salt thereof in an amount of 1–5 moles per mole of the amine derivative in the presence of an inert solvent at 20°–150° C., preferably 40°–100° C. Examples of the halogen atom indicated by $A^2$ in the compound (6) include chlorine, bromine and iodine atoms. Of these, the chlorine atom is more preferred. Specific examples of the compound (6) or salt thereof include sodium chloroacetate, sodium 3-chloro-2-hydroxypropanesulfonate, sodium 3-chloropropionate and sodium 4-chloro-n-butyrate. Of these, sodium chloroacetate and sodium 3-chloro-2-hydroxypropanesulfonate are more preferred. Examples of the inert solvent used herein include polar solvents such as water, methanol, ethanol, isopropanol, dimethylformamide and dimethyl sulfoxide, and the like. These solvents may be used either singly or in any combination thereof. However, water, a lower alcohol or a mixed solvent of water and a lower alcohol is preferred.

When the compound (6) is used in excess to the amine derivative (5) in this reaction, the following quaternized product (1f) is formed.

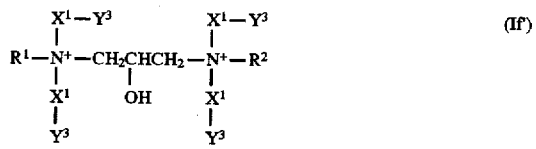

wherein $R^1$, $R^2$, $X^1$ and $Y^3$ have the same meaning as defined above.

After completion of the reaction, the reaction mixture may contain, in addition to the intended compound (1a) according to the present invention, inorganic salts, an unreacted amine derivative (5), an addition compound of the amine derivative (5) and the compound (6) in an amount of 1 mole per mole of the amine derivative (5), and an unreacted compound (6) in some cases. In this case, the intended compound may be purified in the following manner except where the reaction mixture can be used as it is. As a purification method, may be used a method known per se in the art, for example, solvent fractionation, ion exchange chromatography, recrystallization, electrodialysis or the like. Although the intended product obtained may be isolated as a free base, it may be subjected to salt exchange by a usual means such as neutralization with a desired basic substance, thereby isolating it in the form of the desired salt.

[Reaction Scheme b]

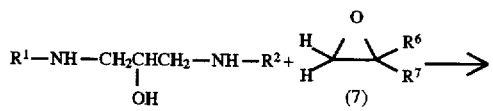

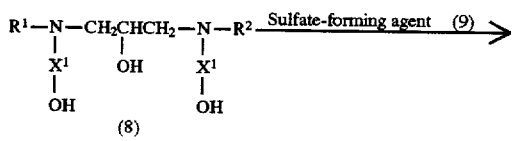

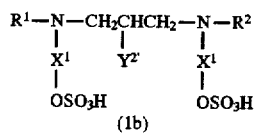

wherein $R^6$ and $R^7$ are identical with or different from each other and mean individually a hydrogen atom, or an alkyl or alkenyl group which may be substituted by a hydroxyl or carboxyl group, $Y^{2'}$ denotes a hydroxyl group or a sulfuric acid residue, and $R^1$, $R^2$ and $X^1$ have the same meaning as defined above.

More specifically, a compound (1b) according to the present invention is prepared by reacting the amine derivative (5) with an epoxy compound (7), reacting the resulting aminoalcohol (8) with a sulfate-forming agent (9) and optionally neutralizing the reaction product with a basic substance.

The reaction of the amine derivative (5) with the epoxy compound (7) is preferably conducted, for example, by reacting the amine derivative (5) with the epoxy compound (7) in an amount of 2–5 moles per mole of the amine derivative in the presence of an inert solvent at a temperature of preferably 100°–200° C., most preferably 130°–180° C. No particular limitation is imposed on the inert solvent used in this reaction so far as it is an aprotic solvent. However, lower hydrocarbons, aromatic hydrocarbons, ethers, halogenated hydrocarbons and the like are preferred in view of price and solubility. This reaction is preferably performed in a pressure vessel such as an autoclave in view of the boiling points of the epoxy compound (7) and the inert solvent used. The epoxy compound (7) is preferably ethylene oxide or propylene oxide because it is cheap, with ethylene oxide being particularly preferred.

The subsequent reaction of the thus-obtained aminoalcohol (9) with the sulfate-forming agent (9) such as $ClSO_3H$ or $SO_3$ is preferably conducted in a temperature range of from $-75°$ C. to $150°$ C. in an inert solvent or without any solvent. The amount of $ClSO_3H$ or $SO_3$ to be used is preferably 1–3 moles per mole of the aminoalcohol (9). Neutralization which is optionally conducted after completion of this reaction is performed by causing a basic substance such as sodium hydroxide, potassium hydroxide, lithium hydroxide, magnesium hydroxide, calcium hydroxide, ammonia, trimethylamine, triethylamine, tributylamine, alkanolamine (monoethanolamine, diethanolamine, triethanolamine or the like), lysine, arginine or choline, preferably, an alkali metal hydroxide such as sodium hydroxide or potassium hydroxide to react in a desired amount according to the intended neutralization degree.

In the above reaction scheme, the reaction of the amine derivative (5) and the epoxy compound (7) may form, as a by-product, a small amount of a compound represented by the following formula:

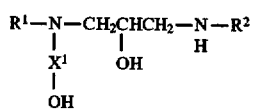

and the reaction of the aminoalcohol (9) and the sulfate-forming agent may form, as by-products, compounds represented by the following formulae:

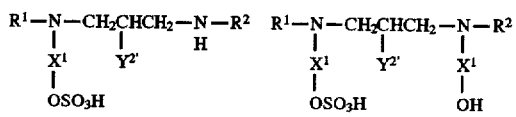

The reaction product may be used in various applications as it is. However, if a higher-purity product is required, it may be purified for use by a method known per se in the art, for example, recrystallization, column chromatography, distillation or the like.

[Reaction Scheme c]

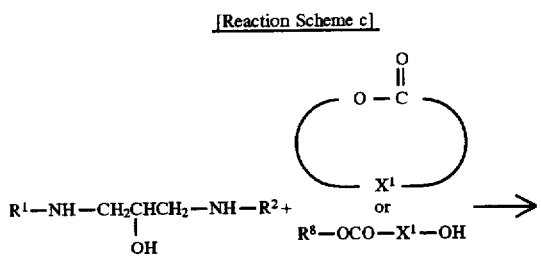

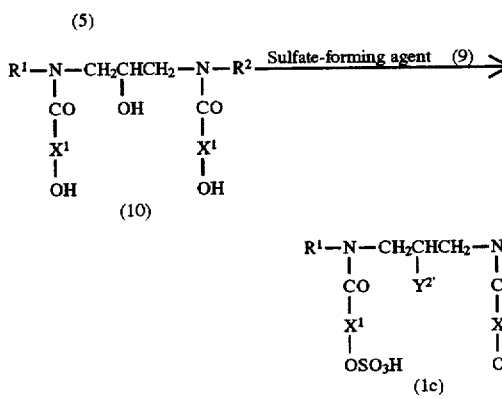

wherein $R^8$ means a hydrogen atom or an alkyl group which may have a substituent group, and $R^1$, $R^2$, $X^1$ and $Y^{2'}$ have the same meaning as defined above.

More specifically, a compound (1c) according to the present invention is prepared by reacting the amine derivative (5) with a lactone or a hydroxycarboxylic acid, reacting the resulting amidoalcohol (10) with a sulfate-forming agent (9) and optionally neutralizing the reaction product with a basic substance.

The reaction of the amine derivative (5) with the lactone or hydroxycarboxylic acid is preferably conducted, for example, by reacting the amine derivative (5) with the lactone or hydroxycarboxylic acid in an amount of 2–5 moles per mole of the amine derivative in an inert solvent or without any solvent at a temperature of preferably 20°–180° C., most preferably 40°–150° C. No particular limitation is imposed on the inert solvent used in this reaction so far as it is an aprotic solvent. However, lower hydrocarbons, aromatic hydrocarbons, ethers, halogenated hydrocarbons and the like are preferred in view of price and solubility. As the lactone and hydroxycarboxylic acid used in this reaction, γ-lactone, δ-lactone, glycolic acid, lactic acid, α-hydroxy acid and the methyl ester and ethyl ester thereof, and the like are preferred because they are cheap.

The reaction of the thus-obtained amidoalcohol (10) with the sulfate-forming agent (9) such as $ClSO_3H$ or $SO_3$ is preferably conducted in a temperature range of from −75° C. to 150° C. in an inert solvent or without any solvent. The amount of $ClSO_3H$ or $SO_3$ to be used is preferably 1–3 moles per mole of the amidoalcohol (10). Neutralization which is optionally conducted after completion of this reaction may be performed in the same manner as in Reaction Scheme b.

In the above reaction scheme, the reaction of the amine derivative (5) and the lactone or hydroxycarboxylic acid may form, as a by-product, a small amount of a compound represented by the following formula:

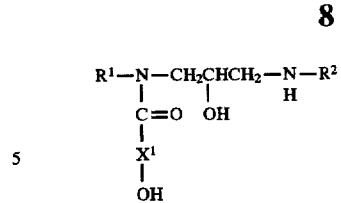

and the reaction of the amidoalcohol (10) and the sulfate-forming agent may form, as by-products, compounds represented by the following formulae:

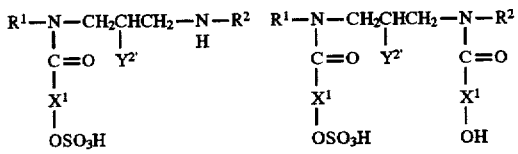

The reaction product may be used in various applications as it is. However, if a higher-purity product is required, it may be purified for use by a method known per se in the art, for example, recrystallization, column chromatography, distillation or the like.

[Reaction Scheme d]

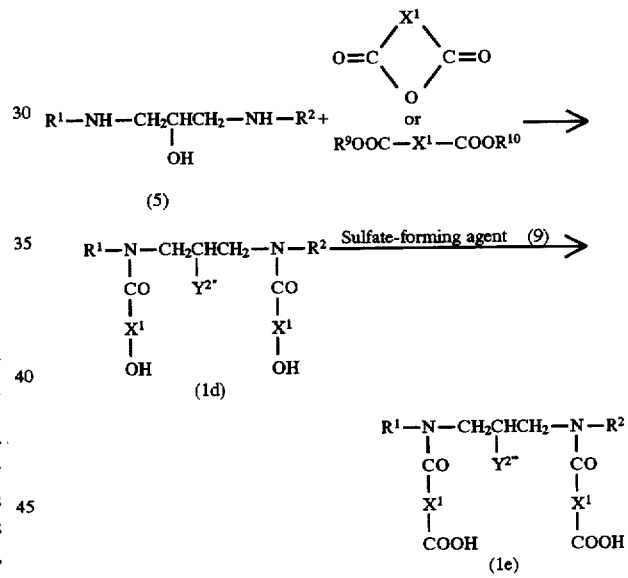

wherein $R^9$ and $R^{10}$ mean individually a hydrogen atom, or an alkyl or alkenyl group which may have a substituent group, $Y^{2'''}$ denotes a hydroxyl group or

$y^{2'''}$ stands for a hydroxyl group or

and $R^1$, $R^2$, $X$ and $X^1$ have the same meaning as defined above.

More specifically, a compound (1d) according to the present invention is prepared by reacting the amine derivative (5) with an acid anhydride, or a dicarboxylic acid or an ester thereof, further hydrolyzing the reaction product if the ester is used, and optionally neutralizing the reaction product or the hydrolyzate with a basic substance. In the case where —CH=CH— is contained in $X^1$ of the resultant compound (1d), a compound (1e) according to the present invention is further prepared by reacting the compound (1d) with a sulfonating agent such as $SO_3$, sodium sulfite or sodium hydrogensulfite, and optionally neutralizing the reaction product with a basic substance.

The reaction of the amine derivative (5) with the acid anhydride is preferably conducted, for example, by reacting the amine derivative (5) with the acid anhydride in an amount of preferably 1.0–5.0 moles per mole of the amine derivative in the presence of a water-free inert solvent at 20°–150° C., preferably 40°–100° C. Examples of the water-free inert solvent used herein include ethers, tetrahydrofuran, benzene and pyridine. In this reaction, the hydroxyl group of the amine derivative (5) reacts with the acid anhydride to form a compound in which $Y^{2-}$ in the formula (1d) is

The reaction of the amine derivative (5) with the dicarboxylic acid or ester thereof is preferably conducted, for example, by reacting the amine derivative (5) with the dicarboxylic acid or ester thereof in an amount of preferably 2.0–5.0 moles per mole of the amine derivative in the presence of an inert solvent at 40°–180° C., preferably 80°–150° C. This reaction is preferably performed while removing an alcohol or water formed. Examples of the inert solvent used in this reaction include hexane, benzene, toluene and xylene.

Incidentally, examples of the alkyl or alkenyl groups indicated by $R^9$ and $R^{10}$ in the formula of the dicarboxylic ester include those having 1–5 carbon atoms. Of these, methyl and ethyl groups are preferred.

In this reaction, an intermediate represented by the general formula (11) is formed if the dicarboxylic ester is used. It is hence necessary to subsequently hydrolyze the intermediate in the presence of an acid or basic catalyst in, for example, a water-containing alcohol.

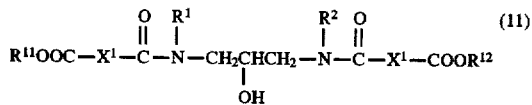

wherein $R^{11}$ and $R^{12}$ mean alkyl or alkenyl groups corresponding to $R^9$ and $R^{10}$, respectively, and $R^1$, $R^2$ and $X^1$ have the same meaning as defined above.

Then, the reaction of the compound (1d) containing —CH=CH— in $X^1$ with the sulfonating agent such as $SO_3$, sodium sulfite or sodium hydrogensulfite is preferably conducted, for example, by reacting the compound (1d) with $SO_3$, sodium sulfite or sodium hydrogensulfite in an amount of 1.0–6.0 moles, preferably 2.0–5.0 moles per mole of the compound (1d) at pH 4.0–11.0, preferably 5.0–8.0 and 30°–100° C., preferably 40°–80° C. in water.

The neutralization of the thus-obtained compounds (1d) and (1e) according to the present invention may be performed in the same manner as in Reaction Scheme b. In these reactions, as with the above-described Reaction Schemes b and c, compounds one amino group of which has been amidated, and the like are formed as by-products. However, the reaction products may be used in various applications as it is. However, if higher-purity products are required, they may be purified for use by a method known per se in the art, for example, recrystallization, column chromatography, electrodialysis or the like.

When n is 0 in the general formula (1), the compound (1f) in which two nitrogen atoms in the compound (1) according to the present invention are quaternized is obtained by reacting the compound (1) with a quaternizing agent. Examples of the quaternizing agent include alkyl (alkenyl) halides which may be substituted by a sulfonic, carboxyl or hydroxyl group and have 1–6 carbon atoms, benzyl halides and alkylene oxides or salts thereof. Of these, the alkyl halides are more preferred. Examples of the alkyl group in these compounds include methyl, ethyl, n-propyl, n-butyl, and isopropyl groups. Examples of the halogen include chlorine, bromine and iodine. Of these compounds, methyl chloride is particularly preferred.

The 2-hydroxypropanediamine derivatives according to the present invention, which are represented by the general formula (1), have excellent detergency and foaming power and hence can be used in applications making good use of these properties, for example, various detergents such as skin and hair detergent compositions, dishwashing detergents, and laundry detergents. No particular limitation is imposed on the amount of the compound (1) according to the present invention to be incorporated in that case. However, it may be used in a range of 0.1–50 wt. % according to the intended application thereof.

These detergent compositions according to the present invention may optionally contain various known surfactants, moisturizers, germicides, emulsifying agents, thickeners, pearly luster-imparting agents, divalent metal ion sequestrants, alkalifying agents, inorganic salts, resoiling preventives, enzymes, available chlorine scavengers, reducing agents, bleaching agents, fluorescent dyes, solubilizing agents, perfume bases, caking preventives, enzyme activators, antioxidants, antiseptics, coloring matter, bluing agents, bleaching activators, enzyme stabilizers, phase modifiers, penetrating agents, and the like.

As the surfactants, may be used anionic surfactants, nonionic surfactants, amphoteric surfactants and cationic surfactants. The anionic surfactants are usually incorporated for the purpose of improving detergency, foaming power and a feel upon use. Examples thereof include higher fatty acid salts, alkylsulfates, alkyl ether sulfates, alkylsulfonates, α-olefinsulfonates, alkylbenzenesulfonates, alkanoylisothionates, alkylsuccinates, alkylsulfosuccinates, N-alkanoylsarcosinates, alkylphosphates, alkyl ether phosphates and alkyl ether carboxylates. The alkyl and acyl groups of these anionic surfactants generally have 8–20 carbon atoms, and may be converted to unsaturated groups. The alkyl ether sulfates, alkyl ether phosphates and alkyl ether carboxylates may contain 1–10 ethylene oxide or propylene oxide units per molecule. However, they preferably contain 2–3 ethylene oxide units per molecule. Examples of the salts of these anionic surfactants include the sodium, magnesium, ammonium and mono-, di- and triethanolamine salts.

The nonionic surfactants are usually incorporated for the purpose of improving detergency and a feel upon use. Examples thereof include polyoxyalkylene alkyl ethers, polyoxyalkylene phenyl ethers, mono- or dialkylalkanolamides or alkylene oxide adducts thereof, alkyl polyglycosides and monoglycerides. The alkyl and acyl groups of these nonionic surfactants generally have 8–20 carbon atoms, and may be converted to unsaturated groups. The polyoxyalkylene groups thereof include polyoxyethylene, polyoxypropylene and a mixed type thereof, and their condensation degree is generally 6–30.

Examples of the amphoteric surfactants include long-chain alkyl-dimethylcarboxymethylbetaines and sulfobetaines. Examples of the cationic surfactants include long-chain alkyl-trimethylammonium salts and di-long-chain-alkyl-dimethylammonium salts.

These surfactants are incorporated collectively with the compound (1) according to the present invention in an amount of generally 0.5–60 wt. % of the detergent composition. In particular, when the detergent composition is provided in the form of powder, they are preferably incorporated in an amount of 10–45 wt. %. When the detergent composition is provided in the form of liquid, they are preferably incorporated in an amount of 20–50 wt. %. Further, when the detergent composition is provided as a bleaching detergent, the surfactants are generally incorporated in an amount of 1–10 wt. %, preferably 1–5 wt. %.

As the moisturizers, may be used glycerin, ethylene glycol, propylene glycol, 1,3-butylene glycol and the like.

As the thickeners, may be used polyacrylic acid, crosslinked polymers of acrylic acid, copolymers of acrylic acid and a hydrophobic monomer, copolymers of a carboxylic acid-containing monomer and an acrylic ester, crosslinked copolymers of acrylic acid and an acrylic ester, ethylene glycol ester or polyethylene glycol ester (for example, fatty acid ester thereof), and heteropolysaccharide gums.

The pearly luster-imparting agents may be selected from $C_{16-22}$ fatty acids, $C_{16-22}$ esters of a fatty acid and an alcohol, and $C_{16-22}$ fatty acid esters containing elements such as alkylene glycol units. Examples of suitable alkylene glycol units include ethylene glycol and propylene glycol. However, polyalkylene glycols may also be used. Examples of suitable polyalkylene glycols include polyethylene glycol and polypropylene glycol.

As the divalent metal ion sequestrants, may be used condensed phosphates such as tripolyphosphates, pyrophosphates and orthophosphates, aluminosilicates such as zeolite, synthetic layer lattice silicates, nitrilotriacetates, ethylenediaminetetraacetates, citrates, isocitrates, polyacetalcarboxylates and the like.

The divalent metal ion sequestrants are incorporated in an amount of 0–50 wt. %, preferably 5–40 wt. %. It is more preferable to use a divalent metal ion sequestrant containing no phosphorus.

As the alkalifying agents and inorganic salts, are used silicates, carbonates, sesquicarbonates, sulfates, alkanolamines and the like. These components are incorporated in an amount of 0–80 wt. %.

As the resoiling preventives, are used polyethylene glycol, polyacrylates, polyacrylic acid copolymers such as acrylic acid-maleic acid copolymers, polyvinyl alcohol, polyvinyl pyrrolidone, carboxymethylcellulose and the like. A part of the resoiling preventives may also be used as divalent metal ion sequestrant. The resoiling preventives are incorporated in an amount of 0–10 wt. %, preferably 1–5 wt. %.

As the enzymes, may be used cellulase, α-amylase, pullulanase, lipase, hemicellulase, β-glycosidase, glucose oxidase, cholesterol oxidase, protease and the like.

Examples of the scavengers for available chlorine in tap water include ammonium sulfate, urea, guanidine hydrochloride, guanidine carbonate, guanidine sulfamate, thiourea dioxide, monoethanolamine, diethanolamine, triethanolamine, glycine, amino acids typified by sodium glutamate and proteins such as bovine serum albumin and casein, and besides hydrolysis of proteins, meat extracts and fish meat extracts. Examples of the reducing agents include alkali metal salts and alkaline earth metal salts such as thiosulfates, sulfites and dithionites thereof, and Rongalit C. Sulfites are particularly preferred and serve to stabilize the enzymes in washing liquid.

Examples of the bleaching agent include percarbonates, perborates, zinc or aluminum sulfonated phthalocyanine, and hydrogen peroxide. When they are used in a bleaching detergent, sodium peroxide is particularly effective. Its amount to be incorporated is preferably 1–95 wt. %, more preferably 5–95 wt. %, most preferably 20–95 wt. %.

Examples of the fluorescent dyes include fluorescent dyes used generally in detergents. In the case of a liquid detergent, a solubilizing agent, for example, a lower alcohol such as ethanol, a benzenesulfonate, a lower alkylbenzenesulfonate such as p-toluenesulfonate, glycerin, or a polyol such as propylene glycol may be incorporated.

The detergent compositions according to the present invention can be prepared by using the compound (1) according to the present invention in combination with the above-described known components in accordance with a method known per se in the art. The form of the detergents may be selected according to the intended application, and the detergents may be prepared in the form of, for example, liquid, powder or granules.

EXAMPLES

The present invention will hereinafter be described more specifically by the following examples. However, it should be born in mind that the invention is not limited to these examples. Example 1

A reactor was charged with 40.2 g (0.108 mole) of bis-(1,3-decylamino)propan-2-ol, 260 g of ethanol and 100 g of water, and the contents were heated to 50° C. To the mixture, was added a solution with 50.3 g (0.432 mole) of sodium monochloroacetate dissolved in 100 g of ethanol and 70 g of water, thereby conducting a reaction for 20 hours under refluxing while keeping pH 8–10 with aqueous sodium hydroxide. After completion of the reaction, the solvent was distilled off, and the residue was washed with chloroform to remove unreacted sodium monochloroacetate and salts such as sodium chloride secondarily produced. After this, the product was purified by column chromatography on silica gel until a single spot was shown by thin-layer chromatography, thereby obtaining 23 g of 2,6-didecyl-4-hydroxy-2,6-diaza-1,7-heptanedicarboxylic acid as white powder (isolation yield: 44%).

This product gave a single peak in HPLC (column: RP-18 (product of Merck Co.)) measurement making use of a mixed solvent of methanol/$H_2O$=80/20 as an eluent.

The $^1$H-NMR data of this product will be shown below.

$^1$H-NMR ($D_2O$): δ(ppm) $D_2O$ standard (4.75) 0.82 (triplet,6H,a), 1.24 (broad singlet,28H,b), 1.57 (broad singlet,4H,c), 2.80–3.09 (complicated multiplet,8H,d) 3.40 (singlet,4H,e), 4.02 (broad singlet,1H,f).

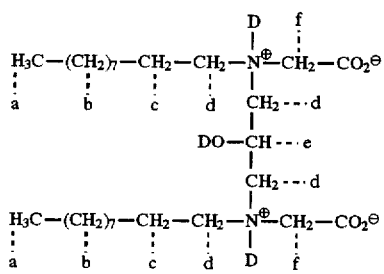

Example 2

A reactor was charged with 40 g (0.13 mole) of bis-(1,3-octylamino)propan-2-ol, 150 g of ethanol and 70 g of water, and the contents were heated to 50° C. To the mixture, was added a solution with 52 g (0.44 mole) of sodium monochloroacetate dissolved in 100 g of ethanol and 70 g of water, thereby conducting a reaction for 26 hours under refluxing while keeping pH 8–10 with aqueous sodium hydroxide. After completion of the reaction, the solvent was distilled off, and the residue was washed with chloroform to remove unreacted sodium monochloroacetate and salts such as sodium chloride secondarily produced. After this, the product was purified by column chromatography on silica gel until a single spot was shown by thin-layer chromatography, thereby obtaining 19 g (isolation yield: 34%) of 2,6-dioctyl-4-hydroxy-2,6-diaza-1,7-heptanedicarboxylic acid as white powder.

This product gave a single peak in HPLC (column: RP-18 (product of Merck Co.)) measurement making use of a mixed solvent of methanol/$H_2O$=80/20 as an eluent.

The $^1$H-NMR data of this product will be shown below.

$^1$H-NMR ($D_2O$): δ(ppm) $D_2O$ standard (4.75) 0.81 (triplet,6H,a), 1.22 (broad singlet,20H,b), 1.55 (broad singlet,4H,c), 2.79–3.11 (complicated multiplet,8H,d) 3.42 (singlet,4H,e), 4.02 (broad singlet,1H,f).

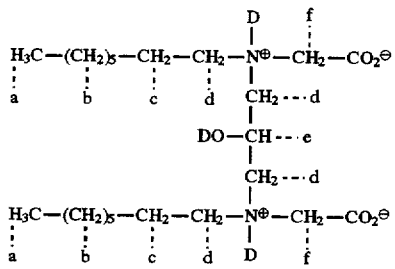

Test Example 1

Test of foaming power

A 1 wt. % aqueous solution or a 0.1 wt. % aqueous solution of each of samples shown in Table 1 was placed in a 800-ml cylinder (diameter: 6.4 cm), and the temperature of the solution was kept at 40° C. The solution was stirred for 5 minutes by means of a reversal stirrer (IHT8S15, manufactured by Japan Serve Co., Ltd.) with the rotation of a stirrer reversed every 5 seconds (maximum revolution: 1,000 rpm). Upon elapsed time of 30 seconds after completion of the stirring, the volume (ml) of foams generated was measured. As a result, it was found that the compounds according to the present invention have excellent foaming power as shown in Table 1.

TABLE 1

| Concentration of aqueous solution | 0.1 wt. % | 1 wt. % |
| --- | --- | --- |
| Compound of Example 1 | 220 | 232 |
| Compound of Example 2 | 212 | 220 |
| Triethanolamine salt of monolauryl phosphate | 150 | 180 |

Example 3

A reactor was charged with 31.8 g (0.086 mole) of bis-(1,3-decylamino)propan-2-ol, 244 g of ethanol and 51 g of water, and the contents were heated to 75° C. To the mixture, was added a solution with 76.7 g (0.390 mole) of sodium 3-chloro-2-hydroxypropane-1-sulfonate dissolved in 361 g of water. While keeping pH 8–10 with aqueous sodium hydroxide, the resulting mixture was maintained for 20 at 75° C. After completion of a reaction, the solvent was distilled off under reduced pressure, and the residue was recrystallized from water-ethanol. The thus-obtained crystals were washed with acetone, thereby obtaining 37.3 g (0.057 mole) of 4,8-didecyl-2,6,10-trihydroxy-4,8-diaza-1,11-undecanedisulfonic acid as white powder.

This product gave a single peak in HPLC (column: RP-18 (product of Merck Co.)) measurement making use of a mixed solvent of methanol/$H_2O$=80/20 as an eluent.

The $^1$H-NMR data of this product will be shown below (Incidentally, a-i in the data indicate the positions in the following chemical formula, by which the respective signals are produced).

$^1$H-NMR ($D_2O$) :δ(ppm) $D_2O$ standard (4.70) 0.79 (triplet,6H,a), 1.20 (broad singlet,28H,b), 1.51 (broad singlet,4H,c), 2.75–3.24 (complicated multiplet,16H,d,e,f,g) 3.98 (broad singlet,1H,h), 4.23 (broad singlet,2H,i).

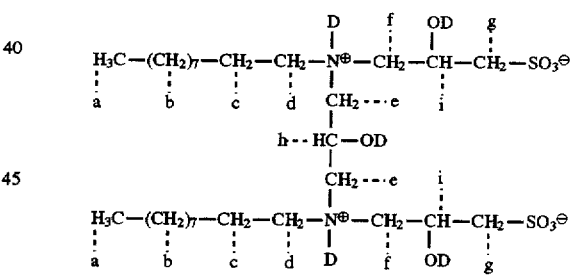

Test Example 2

Test of foaming performance

The foaming performance of 4,8-didecyl-2,6,10-trihydroxy-4,8-diaza-1 11-undecanedisulfonate, which was a compound according to the present invention, and the sodium salt of lauryl ether sulfate as a comparative substance was tested in accordance with the following method. The results are shown in Table 2.

(Method)

1. In an about 800-ml cylinder, is placed 100 ml of a solution of each activator.

2. Reversal stirring of the solution is carried out for 5 minutes at 40° C.

3. Upon elapsed time of 30 seconds and 5 minutes after leaving the solution at rest, the volume (ml) of foams is measured.

TABLE 2

| Activator | Concentration (wt. %) | Volume of foams pH 7 30 sec→5 min | pH 10 30 sec→5 min |
|---|---|---|---|
| Invention compound | *1 | 0.1 | 220→203 | 193→183 |
| | | 0.01 | 186→167 | 180→159 |
| Comparative compound | *2 | 0.1 | 212→170 | 210→175 |
| | | | 135→77 | 120→70 |

*1: 4,8-Didecyl-2,6,10-trihydroxy-4,8-diaza-1,11-undecane-disulfonic acid.
*2: The sodium salt of lauryl ether sulfate.

As described above, it is understood that the compound according to the present invention has excellent foaming power and foam stability in a wide pH range.

Example 4

Preparation of 3,7-didodecyl-3,7-diaza-1,5,9-nonanetriol

An 1-liter autoclave was charged with 50.2 g (0.12 mole) of 15-hydroxy-13,17-diazanonacosan and 500 ml of xylene, and the contents were heated to 155° C. Into the mixture, was poured 22 g (0.5 mole) of ethylene oxide. The resulting mixture was kept for 6 hours at 155° C., thereby conducting a reaction. After completion of the reaction, the solvent was distilled off under reduced pressure, thereby obtaining 60 g (yield: 99%) of the title compound as a viscous liquid.

Mass spectrometry (FAB ionization method): m/z=515 (M+H)+(M=$C_{31}H_{66}O_3N_2$)

$^1$H-NMR (CDCl$_3$): δ(ppm) 0.85 (triplet,6H,a), 1.21 (broad singlet,36H,b), 1.45 (quintet,4H,c), 2.41–2.70 (complicated multiplet,12H,d,e,g) 3.57 (triplet,4H,h), 3.75 (quintet,1H,f).

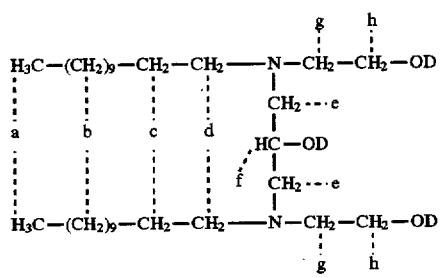

Example 5

Preparation of 3,7-didodecyl-5-hydroxy-3,7-diaza-1,9-nonanedisulfate

A reactor was charged with 18 g (0.035 mole) of 3,7-didodecyl-3,7-diaza-1,5,9-nonanetriol obtained in Example 4 and 135 ml of dichloromethane, to which 5.1 ml (0.077 mole) of chlorosulfonic acid was added dropwise in a nitrogen stream while chilling with ice water. Thereafter, the temperature of the resulting mixture was gradually raised to room temperature, and hydrochloric acid and dichloromethane generated were purged with nitrogen. n-Butanol was added to the residue to dissolve the residue therein. After the solution was washed with water, the solvent was distilled under reduced pressure to obtain 24.8 g of a solid. This solid was then dissolved in water, and the pH of the solution was adjusted to 7.0 with 1N aqueous sodium hydroxide. Thereafter, the solution was subjected to desalting by means of a demineralizer (Microacylizer G3, manufactured by Asahi Chemical Industry Co., Ltd.). The thus-desalted solution was further dried by means of a lyophilizer, thereby obtaining 17.2 g (yield: 85%) of the title compound as white powder.

It was confirmed by thin-layer chromatography (developing solvent: chloroform/methanol=3/1) that this compound shows a single spot (Rf=0.5). An $^1$H-NMR (solvent: CDCl$_3$) chart of this compound is illustrated in FIG. 1. Further, the IR spectrum of this compound was as follows:

IR (KBr briquette method, cm$^{-1}$): 3600–3200 (vO—H), 1390, 1192 (vS=O).

Example 6

Preparation of sodium 3,7-didodecyl-3,7-diaza-1,5,9-nonanetrisulfate

A reactor was charged with 18 g (0.035 mole) of 3,7-didodecyl-3,7-diaza-1,5,9-nonanetriol obtained in Example 4 and 150 ml of dichloromethane, to which 7.7 ml (0.115 mole) of chlorosulfonic acid was added dropwise in a nitrogen stream while chilling with ice water. Thereafter, the temperature of the resulting mixture was gradually raised to room temperature, and hydrochloric acid and dichloromethane generated were purged with nitrogen. Water was added to the residue to dissolve the residue therein, and the pH of the solution was adjusted to 7.0 with 1N aqueous sodium hydroxide. Thereafter, the solution was subjected to desalting by means of a demineralizer (Microacylizer G3, manufactured by Asahi Chemical Industry Co., Ltd.). The thus-desalted solution was further dried by means of a lyophilizer, thereby obtaining 26.7 g (yield: 97%) of the title compound as white powder.

Figure 2:
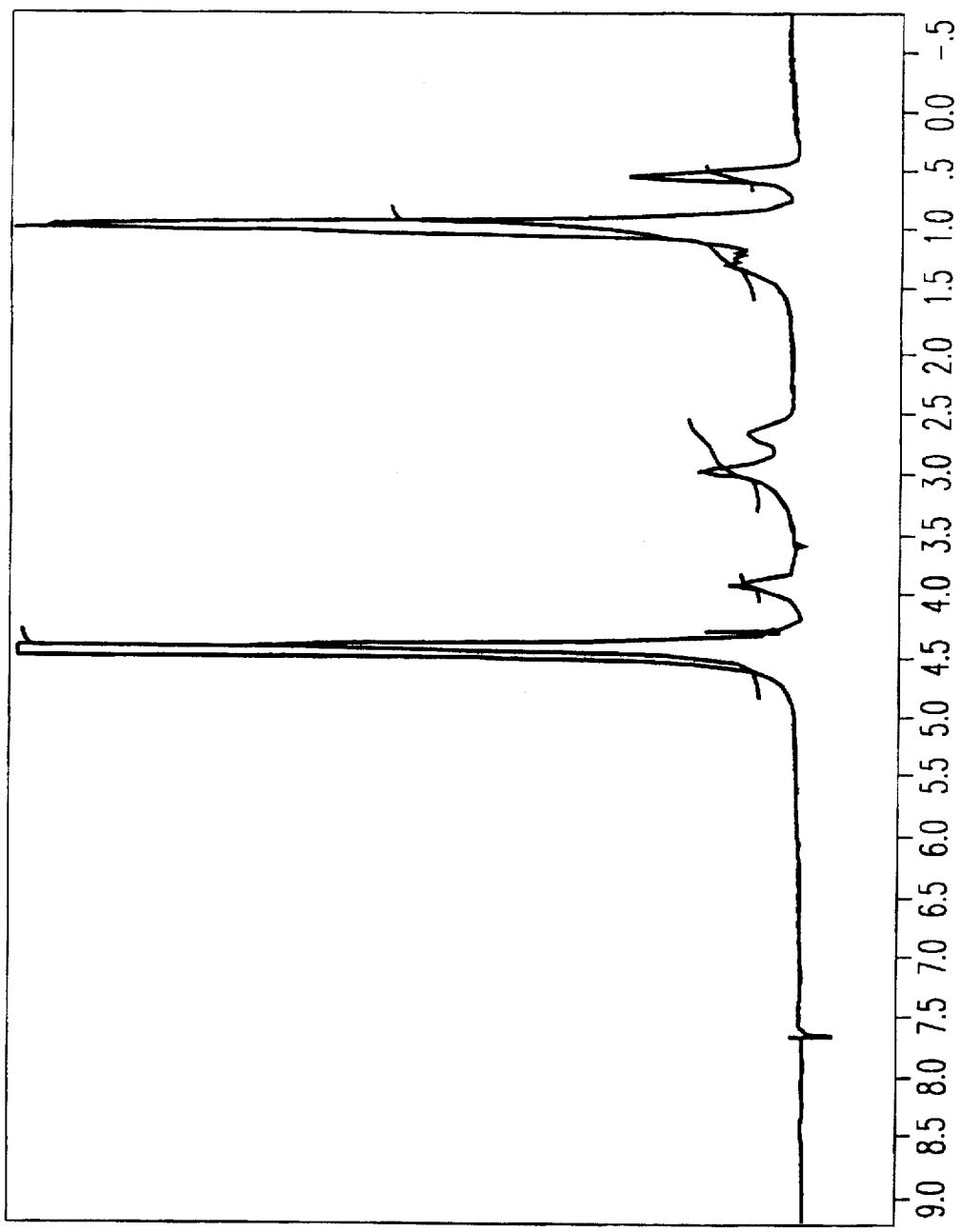
FIG. 2 illustrates an $^1$H-NMR chart of a compound obtained in Example 6.

It was confirmed by thin-layer chromatography (developing solvent: chloroform/methanol=1/1) that this compound shows a single spot (Rf=0.3). An $^1$H-NMR (solvent: D$_2$O) chart of this compound is illustrated in FIG. 2. Further, the IR spectrum of this compound was as follows:

IR (KBr briquette method, cm$^{-1}$): 1390, 1186 (vS=O).

Example 7

Preparation of 5,9-didodecyl-4,10-dioxo-5,9-diaza-1,7,13-tridecanetriol

A reactor was charged with 9.5 g (0.02 mole) of 15-hydroxy-13,17-diazanonacosan and 11.7 g (0.13 mole) of γ-butyrolactone, and the contents were heated to 160° C. and kept for 5 hours at this temperature, thereby reacting them. After completion of the reaction, the product was purified by column chromatography (on 500 g of silica gel, developing solvent: chloroform/methanol=97/3), thereby obtaining 6 g (yield: 45%) of the title compound as a viscous liquid.

Mass spectrometry (FAB ionization method): m/z=600 (M+H)+(M=$C_{35}H_{70}O_5N_2$)

$^1$H-NMR (CDCl$_3$): δ(ppm) 0.87 (triplet,6H,a), 1.23 (broad singlet,36H,b), 1.53 (quintet,4H,c), 1.85 (quintet,4H,h), 2.40–2.52 (broad multiplet,4H,g) 3.28–3.40 (broad multiplet,8H,d,e) 3.65 (triplet,4H,j), 4.03 (broad multiplet, 4H,i).

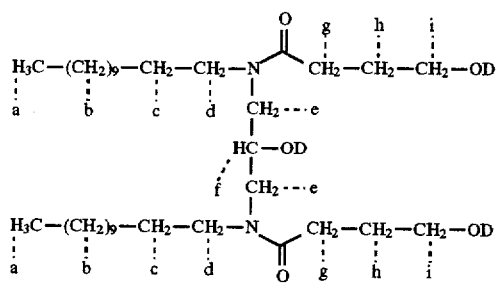
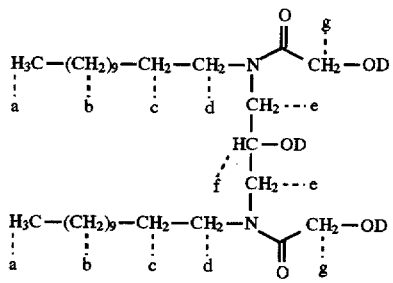

Example 8

Preparation of disodium 5,9-didodecyl-7-hydroxy-4,10-dioxo-5,9-diaza-1,13-tridecanedisulfate A reactor was charged with 6 g (0.01 mole) of 5,9-didodecyl-4,10-dioxo-5,9-diaza-1,7,13-tridecanetriol obtained in Example 7, 4.5 g (0.06 mole) of pyridine and 50 ml of dichloromethane, to which 3 ml (0.02 mole) of chlorosulfonic acid was added dropwise in a nitrogen stream while chilling with ice water. Thereafter, the contents were kept at 0°–5° C. and continuously stirred. After completion of a reaction, the reaction mixture was treated with 11 g (0.06 mole) of sodium methylate (28% methanol solution). The solvent was then distilled off under reduced pressure, and the residue was dissolved in water. The resulting solution was subjected to desalting by electrodialysis. The thus-desalted solution was lyophilized, thereby obtaining 3.3 g (yield: 41%) of the title compound as white powder.

Figure 3:
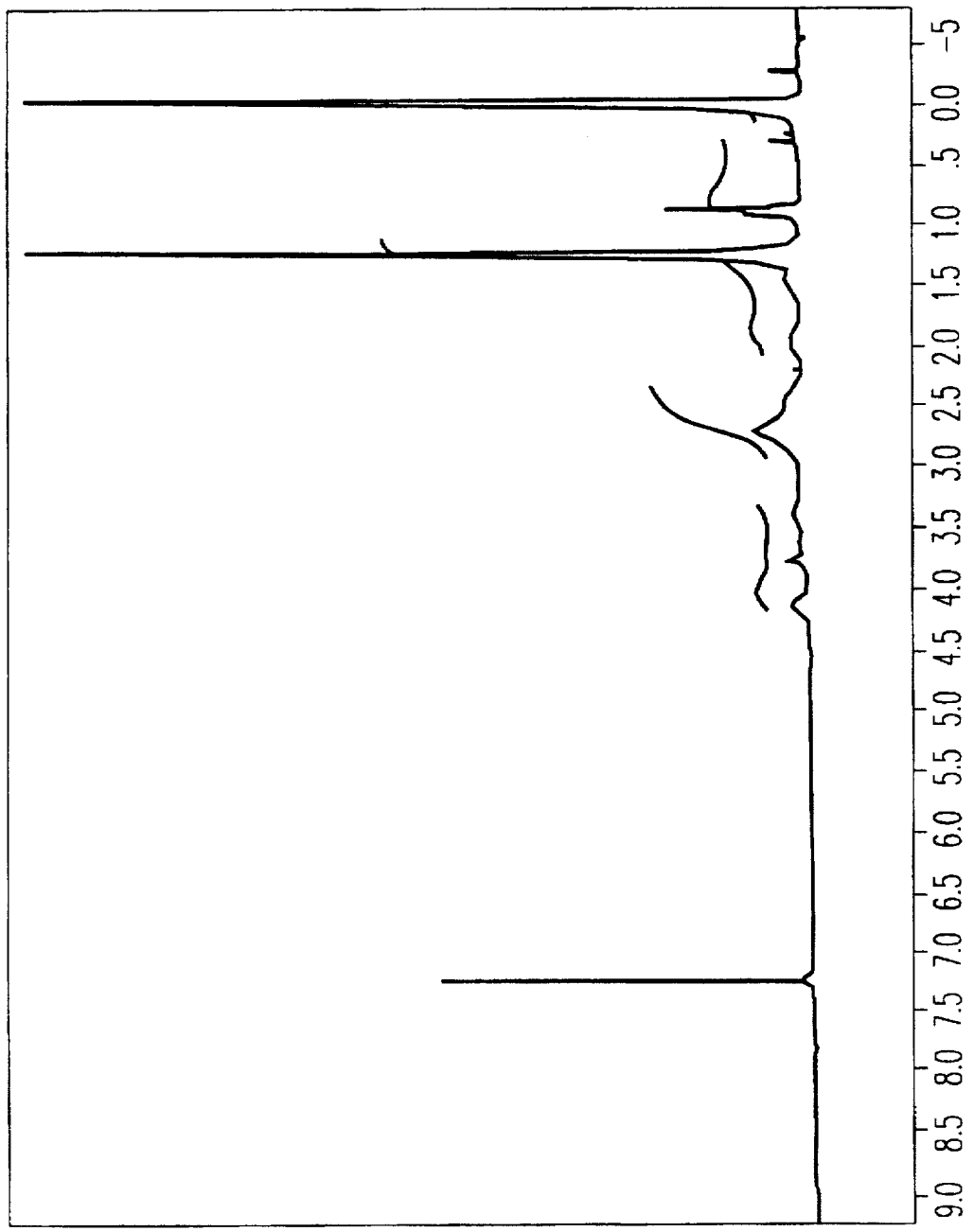
FIG. 3 illustrates an $^1$H-NMR chart of a compound obtained in Example 8.

It was confirmed by thin-layer chromatography (developing solvent: chloroform/methanol=2/1) that this compound shows a single spot (Rf=0.3). An $^1$H-NMR (solvent: CDCl$_3$) chart of this compound is illustrated in FIG. 3. Further, the IR spectrum of this compound was as follows:

IR (KBr briquette method, cm$^{-1}$): 3620–3300 (vO—H), 1690(vC=O), 1392, 1188 (vS=O).

Example 9

Preparation of 3,7-didodecyl-2,8-dioxo-3,7-diaza-1,5,9-nonanetriol

A reactor was charged with 10.7 g (0.03 mole) of 15-hydroxy-13,17-diazanonacosan, 50 ml of toluene and 7.1 ml (0.07 mole) of ethyl glycolate, and the contents were heated to 100° C. and continuously stirred for 7.5 hours while purging ethanol formed with a nitrogen stream. After completion of a reaction, the solvent was distilled off under reduced pressure, and the residue was purified by column chromatography (on 200 g of silica gel, developing solvent: chloroform/methanol=100/1), thereby obtaining 13 g (yield: 96%) of the title compound as a viscous liquid.

Mass spectrometry (FAB ionization method): m/z=543 (M+H)+(M=C$_{31}$H$_{62}$O$_5$N$_2$)

$^1$H-NMR (CDCl$_3$): δ(ppm) 0.82 (triplet,6H,a), 1.28 (broad singlet,36H,b), 1.49–1.60 (broad multiplet,4H,c), 3.18 (triplet,4H,d), 4.05(broad multiplet,1H,f), 4.20 (singlet, 4H,g).

Example 10

Preparation of disodium 3,7-didodecyl-5-hydroxy-2,8-dioxo-3,7-diaza-1,9-nonanedisulfate A reactor was charged with 10.8 g (0.021 mole) of 3,7-didodecyl-2,8-dioxo-3,7-diaza-1,5,9-nonanetriol obtained in Example 9 and 50 ml of dichloromethane, to which 3 ml (0.04 mole) of chlorosulfonic acid was added dropwise over 20 minutes in a nitrogen stream while chilling with ice water. Thereafter, the temperature of the resulting mixture was gradually raised to room temperature, and hydrochloric acid and dichloromethane generated were purged with a nitrogen stream. Water was added to the residue to dissolve the residue therein, and the pH of the solution was adjusted to 7 with 1N aqueous sodium hydroxide. After the thus-treated solution was subjected to desalting by electrodialysis, the thus-desalted solution was lyophilized, thereby obtaining 11.8 g (yield: 79%) of the title compound as white powder.

Figure 4:
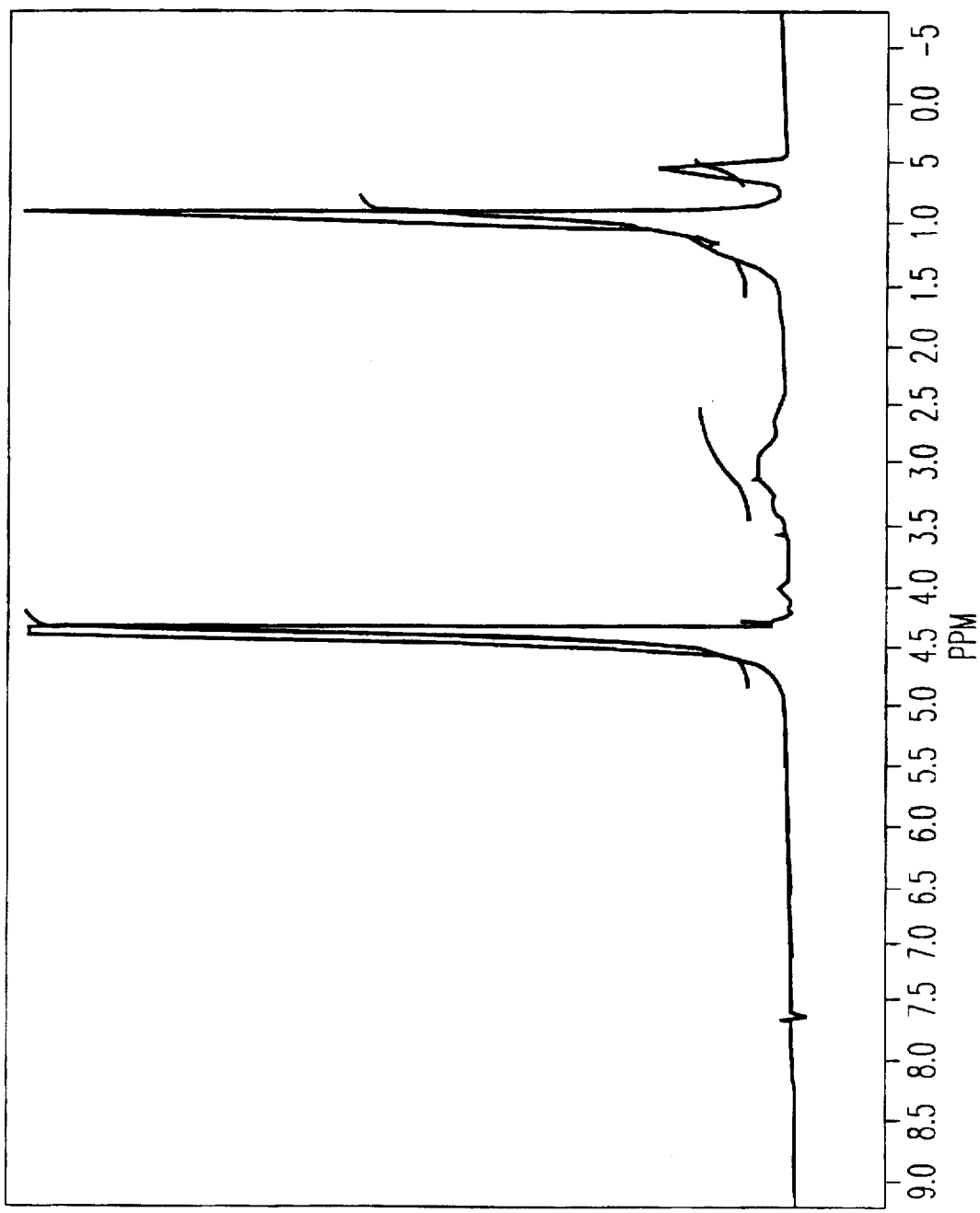
FIG. 4 illustrates an $^1$H-NMR chart of a compound obtained in Example 10.

It was confirmed by thin-layer chromatography (developing solvent: chloroform/methanol=3/1) that this compound shows a single spot (Rf=0.2). An $^1$H-NMR (solvent: D$_2$O) chart of this compound is illustrated in FIG. 4. Further, the IR spectrum of this compound was as follows:

IR (KBr briquette method, cm$^{-1}$): 3600–3200 (vO—H), 1658(vC=O), 1385, 1195 (vS=O).

Example 11

Preparation of trisodium 3,7-didodecyl-2,8-dioxo-3,7-diaza-1,5,9-nonanetrisulfate A reactor was charged with 28 g (0.05 mole) of 3,7-didodecyl-2,8-dioxo-3,7-diaza-1,5,9-nonanetriol obtained in Example 9 and 100 ml of dichloromethane, to which 11 ml (0.16 mole) of chlorosulfonic acid was added dropwise over 20 minutes in a nitrogen stream while chilling with ice water. Thereafter, the temperature of the resulting mixture was gradually raised to room temperature, and hydrochloric acid and dichloromethane generated were purged with a nitrogen stream. Water was added to the residue to dissolve the residue therein, and the pH of the solution was adjusted to 7 with 1N aqueous sodium hydroxide. After the thus-treated solution was subjected to desalting by electrodialysis, the thus-desalted solution was lyophilized, thereby obtaining 28 g (yield: 66%) of the title compound as white powder.

Figure 5:
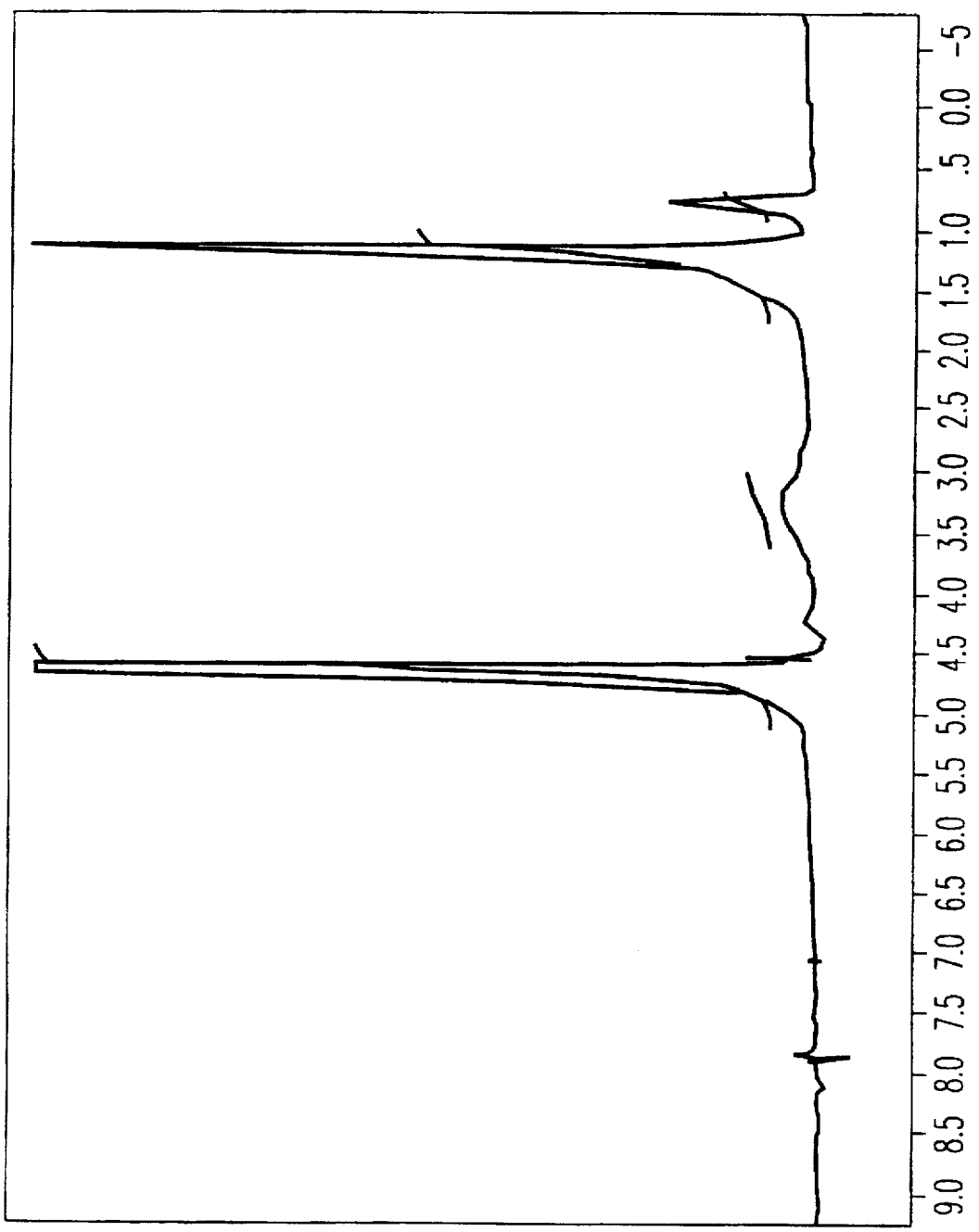
FIG. 5 illustrates an $^1$H-NMR chart of a compound obtained in Example 11.

It was confirmed by thin-layer chromatography (developing solvent: chloroform/methanol=1/1) that this compound shows a single spot (Rf=0.3). An $^1$H-NMR (solvent: D$_2$O) chart of this compound is illustrated in FIG. 5. Further, the IR spectrum of this compound was as follows:

IR (KBr briquette method, cm$^{-1}$): 1390, 1185(vS=O), 1660 (vC=O).

Example 12

A reactor was charged with 22.2 g (0.06 mole) of bis-(1,3-decylamino)propan-2-ol, 19.8 g (0.18 mole) of succinic anhydride and 300 ml of anhydrous ether, and the contents were refluxed for 5 hours. After completion of a reaction, insoluble succinic anhydride in an excess amount was removed by filtration, and an ether layer was washed with water. The ether was distilled off under reduced pressure, thereby obtaining 34 g (0.06 mole) of 4,8-didecyl-3,9-dioxo-6-hydroxy-4,8-diaza-1,11-undecanedicarboxylic acid as a glassy solid.

After adjusted to pH 10 with sodium hydroxide, this compound gave a single peak in HPLC measurement [column: RP-18 (product of Merck Co.), eluent: methanol/water=80/20].

The $^1$H-NMR data of this product will be shown below.

$^1$H-NMR (CDCl$_3$): δ(ppm) TMS standard 0.88 (triplet, 6H,a), 1.26 (broad singlet,28H,b), 1.47 (broad singlet,4H,c), 2.64 (complicated multiplet,8H,g,h), 3.3–3.9 (complicated multiplet,9H,d,e,f).

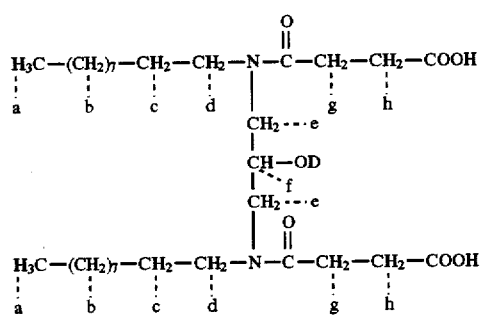

Example 13

A reactor was charged with 17.04 g (0.04 mole) of bis-(1,3-decylamino)propan-2-ol, 19.6 g (0.2 mole) of maleic anhydride and 200 ml of anhydrous ether, and the contents were refluxed for 3 hours. After completion of a reaction, the ether was distilled off under reduced pressure, and ethyl acetate was added to the residue to dissolve the residue therein. The resulting solution was washed with water. Thereafter, ethyl acetate was distilled off, thereby obtaining 25 g (0.04 mole) of 4,8-didodecyl-3,9-dioxo-6-hydroxy-4,8-diaza-1,10-undecene-1,11-dicarboxylic acid as a glassy solid.

After adjusted to pH 10 with sodium hydroxide, this compound gave a single peak in HPLC measurement [column: RP-18 (product of Merck Co.), eluent: methanol/water=75/25].

The $^1$H-NMR data of this product will be shown below.

$^1$H-NMR (CDCl$_3$): δ(ppm) TMS standard 0.89 (triplet, 6H,a), 1.27 (broad singlet,36H,b), 1.56 (broad singlet,4H,c), 3.25–3.58 (complicated multiplet,8H,d,e), 3.8–3.95 (complicated multiplet,1H,f), 6.1–6.65 (complicated multiplet,4H,g,h).

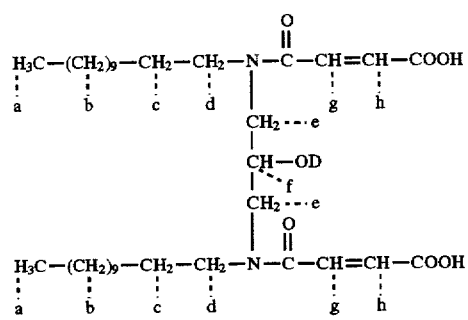

Test Example 3

The foamability of sodium 4,8-decyl-3,9-dioxo-6-hydroxy-4,8-diaza-1,11-undecanedicarboxylate obtained in Example 12,sodium 4,8-didodecyl-3,9-dioxo-6-hydroxy-4,8-diaza-1,10-undecene-1,11-dicarboxylate and sodium laurate as a comparative compound was tested in accordance with the following method.

(Testing method)

First, 100 ml of an aqueous solution (0.1 wt. %) of each compound was placed in an about 800-ml cylinder. Reversal stirring of the solution was then conducted for 5 minutes at 40° C. Thereafter, the solution was left at rest to measure the volume (ml) of foams generated upon elapsed time of 30 seconds and 5 minutes after the stopping of stirring. The results are shown in Table 3.

TABLE 3

| Activator | Concentration (wt. %) | Volume of foams (ml) pH 7, 30 sec→5 min |
|---|---|---|
| Compound of Example 12 | 0.1 | 206→108 |
| Compound of Example 13 | 0.1 | 172→88 |
| Sodium laurate | 0.1 | 76→35 |

Table 3 revealed that the compounds according to the present invention have excellent foamability.

Example 14

A reactor was charged with 10.65 g (0.025 mole) of bis-(1,3-dodecylamino)propan-2-ol, 100 ml of toluene and 117 ml (0.01 mole) of diethyl tartarate. While removing ethanol formed, a reaction was conducted for 20 hours at 80° C. After completion of the reaction, succinic anhydride in an excess amount was removed by washing with water, and a toluene layer was dried over anhydrous sodium sulfate. Thereafter, the residue was absolutely dried under reduced pressure, thereby obtaining 18 g (0.024 mole, 97%) of ethyl 4,8-didodecyl-3,9-dioxo-1,2,6,10,11-pentahydroxy-4,8-diaza-1,11-undecanecarboxylate as a viscous liquid.

The $^1$H-NMR data of the compound will be shown below.

$^1$H-NMR (CDCl$_3$): δ(ppm) TMS standard 0.89 (triplet, 6H,a), 1.2–1.3 (complicated multiplet,42H,b,j), 1.63 (broad singlet,4H,c), 3.52 (broad singlet,8H,d,e), 3.7–4.1 (complicated multiplet,5H,i,f), 4.6–4.85 (complicated multiplet,4H,g,h).

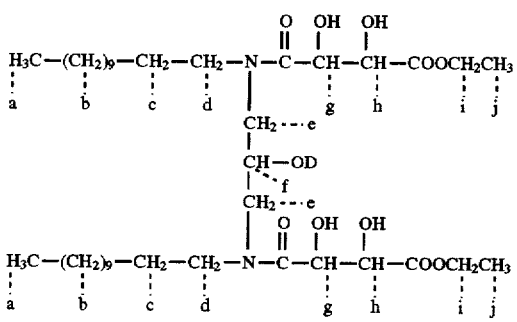

Example 15

Ethyl 4,8-didodecyl-3,9-dioxo-1,2,6,10,11-pentahydroxy-4,8-diaza-1,1-undecanecarboxylate obtained in Example 14 was dissolved in 50 ml of water-ethanol (1:1), and sodium hydroxide (2 g, 0.05 mole) was added to the solution, followed by stirring for 10 hours at 60° C. After completion of a reaction, ethanol in the reaction mixture was distilled off under reduced pressure, and the remaining aqueous solution was lyophilized, thereby obtaining sodium 4,8-didodecyl-3,9-dioxo-1,2,6,10,11-pentahydroxy-4,8,-diaza-1,11-undecanedicarboxylate (quantitative amount) as white powder.

In the IR spectrum (KBr briquette method) of this compound, absorption was observed at 3000–3700 cm$^{-1}$ (O—H) and 1500–1800 cm$^{-1}$ (C=O).

Example 16

A reactor was charged with 12.78 g (0.03 mole) of bis-(1,3-dodecylamino)propan-2-ol, 100 ml of toluene and 30 ml (0.12 mole) of triethyl citrate. While removing ethanol formed, a reaction was conducted for 25 hours at 100° C. After completion of the reaction, toluene was distilled off under reduced pressure, and the residue was purified by column chromatography on silica gel, thereby obtaining 25 g (0.028 mole) of ethyl 5,9-didodecyl-4,10-dioxo-2,7,12-trihydroxy-5,9-diaza-1,2,12,13-tridecanetetracarboxylate as white powder.

The $^1$H-NMR data of the compound will be shown below.

$^1$H-NMR (CDCl$_3$): δ(ppm) TMS standard 0.9 (triplet,6H, a), 1.3 (complicated multiplet,48H,b,j), 1.65 (broad singlet, 4H,c), 2.7–2.9 (complicated multiplet,8H,g,h), 3.45 (broad singlet,8H,d,e), 3.85–4.3 (complicated multiplet,9H,i,f).

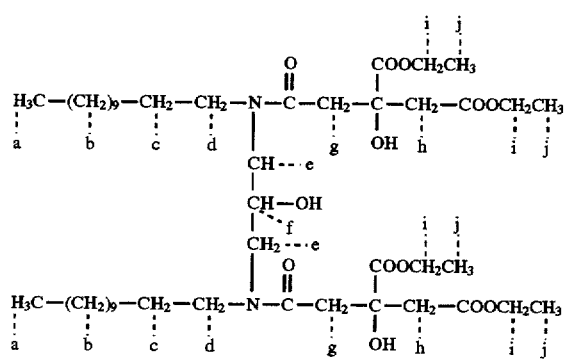

Example 17

Ethyl 5,9-didodecyl-4,10-dioxo-2,7,12-trihydroxy-5,9-diaza-1,2,12,13-tridecanetetracarboxylate obtained in Example 16 was dissolved in 50 ml of water-ethanol (1:1), and 2.0 g (0.05 mole) of sodium hydroxide was added to the solution, followed by stirring for 5 hours at 60° C. After completion of a reaction, ethanol in the reaction mixture was distilled off under reduced pressure, and 2 g of sodium hydroxide was further added to the remaining aqueous solution to lyophilize it, thereby obtaining sodium 5,9-didodecyl- 4,10-dioxo-2,7,12-trihydroxy-5,9,-diaza-1,2,12, 13-tridecanetetracarboxylate (quantitative amount) as white powder.

In the IR spectrum (KBr briquette method) of this compound, absorption was observed at 3000–3700 cm$^{-1}$ (O—H) and 1500–1800 cm$^{-1}$ (C=O).

Example 18

A reactor was charged with 21.8 g (0.035 mole) of 4,8-didodecyl-3,9-dioxo-6-hydroxy-4,8-diaza-1,10-undecene-1,11-dicarboxylic acid and 70 ml of an aqueous solution of 9.7 g (0.077 mole) of sodium sulfite. The pH of the reaction mixture was kept at 5–6 to stir it for 2 hours at 60° C. After completion of a reaction, the reaction mixture was adjusted to pH 7 with 1N aqueous sodium hydroxide, and sodium sulfite in an excess amount was removed by electrodialysis. Thereafter, the thus-treated reaction product was lyophilized to obtain 30 g of sodium 4,8-didodecyl-3,9-dioxo-6-hydroxy-1,11-dicarboxy-4,8-diaza-1,11-undecanedisulfonate as white powder.

The mass spectrometry (FAB ionization method) of 4,8-didodecyl-3,9-dioxo-6-hydroxy-1,11-dicarboxy-4,8-diaza-1,11-undecanedisulfonic acid obtained by treating the above compound with 1N hydrochloric acid and represented by the following formula:

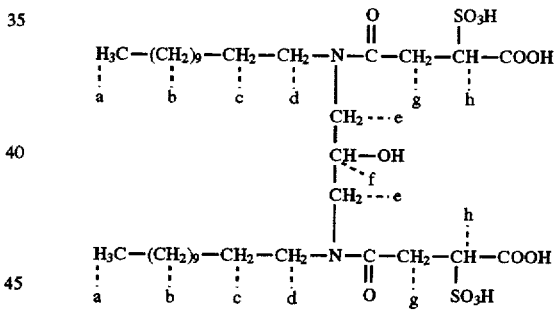

showed a peak of m/z=783 (M+H). The result of its $^1$H-NMR was as follows:

$^1$H-NMR (CDCl$_3$):δ(ppm)TMS standard 0.88 (triplet,6H, a), 1.26 (broad singlet,36H,b), 1.54 (broad singlet,4H,c), 2.74 (complicated multiplet,2H,g) 3.25–3.9 (complicated multiplet, 11H,d,e,f,h).

Example 19

A reactor was charged with 20 g (0.053 mole) of 9-hydroxy-7,11-diaza-tricosane, 13 g (0.130 mole) of succinic anhydride and 300 ml of anhydrous ether, and the contents were refluxed for 5 hours. After completion of a reaction, insoluble succinic anhydride in an excess amount was removed by filtration, and an ether layer was washed with water. The ether was distilled off under reduced pressure, thereby obtaining 30 g (0.055 mole) of 4-dodecyl-8-hexyl-3,9-dioxo-6-hydroxy-4,8-diaza-1,11-undecanedicarboxylic acid as a viscous transparent liquid. After adjusted to pH 10 with sodium hydroxide, this compound gave a single peak in HPLC measurement [column:

RP-18 (product of Merck Co.), eluent: methanol/water=80/20]. The $^1$H-NMR data of the compound will be shown below.

$^1$H-NMR (CDCl$_3$): δ(ppm) TMS standard 0.89 (triplet, 6H,a), 1.26 (broad singlet,24H,b), 1.43 (broad singlet,4H,c), 2.60 (complicated multiplet,8H,g,h), 3.29–3.87 (complicated multiplet,9H,d,e,f).

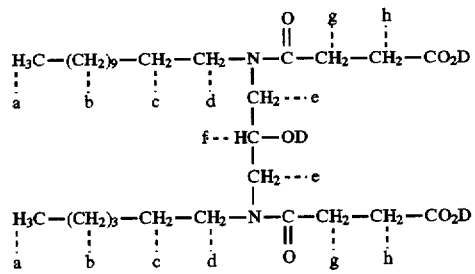

Example 20

A reactor was charged with 21.3 g (0.05 mole) of bis-(1,3-dodecylamino)propan-2-ol, 16.5 g (0.15 mole) of succinic anhydride and 300 ml of anhydrous ether, and the contents were refluxed for 5 hours. After completion of a reaction, the ether was distilled off under reduced pressure, thereby obtaining 37.8 g (quantitative amount) of 6-(3-carbohydroxy-propanoxy)-4,8-didodecyl-3,9-dioxo-4,8-diaza-1,11-undecanedicarboxylic acid. This compound gave a single peak in HPLC measurement [column: RP-18 (product of Merck Co.), eluent: methanol/water=90/10, 50 mM ammonium acetate].

$^1$H-NMR (CDCl$_3$): δ(ppm) TMS standard 0.89 (triplet, 6H,a), 1.28 (broad singlet,24H,b), 1.55 (broad singlet,4H,c), 2.24–2.82 (complicated multiplet,12H,g,h), 2.90–3.83 (complicated multiplet,9H,d,e,f).

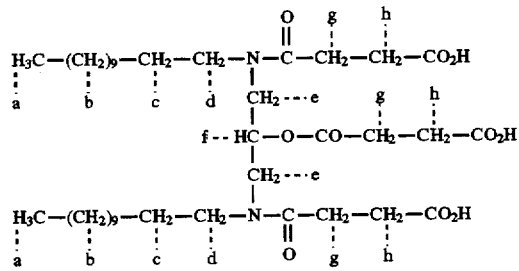

IR (KBr): 3560, 2940, 2860, 1730, 1630, 1560 cm$^{-1}$.

Example 21

A reactor was charged with 40.2 g (0.108 mole) of bis-(1,3-decylamino)propan-2-ol, 260 g of ethanol and 100 g of water, and the contents were heated to 50° C. To the mixture, was added a solution with 62.9 g (0.540 mole) of sodium monochloroacetate dissolved in 150 g of isopropanol and 100 g of water, thereby conducting a reaction for 30 hours under refluxing while keeping pH 8–10. After completion of the reaction, the solvent was distilled off, and the residue was dissolved in chloroform to remove insoluble, unreacted sodium monochloroacetate and salts such as sodium chloride secondarily produced. After this, the product was purified by column chromatography on silica gel until a single spot was shown by thin-layer chromatography, thereby obtaining 20 g (isolation yield: 31%) of 2,6-didecyl-4-hydroxy-2,6-diaza-1,1,7,7-heptanetetracarboxylic acid as white powder.

This product gave a single peak in HPLC (column: RP-18 (product of Merck Co.)) measurement making use of an eluting solution of methanol/H$_2$O=80/20.

The $^1$H-NMR data of this product will be shown below.

$^1$H-NMR (D$_2$O): δ(ppm) D$_2$O standard (4.75) 0.82 (triplet,6H,a), 1.24 (broad singlet,28H,b), 1.57 (broad singlet,4H,c), 2.99–3.32 (complicated multiplet,8H,d) 3.58 (broad singlet,8H,d), 4.02 (broad singlet,1H,e).

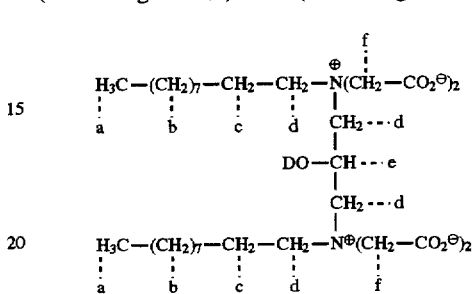

Example 22

A reactor was charged with 10 g (0.023 mole) of 2,6-dioctyl-4-hydroxy-2,6-diaza-1,7-heptanedicarboxylic acid obtained in Example 2 and 20 g of methanol, and the contents were heated to 50° C. Added to them were 8.4 g (0.06 mole) of methyl iodide, thereby conducting a reaction at 60° C. for 14 hours. After completion of a reaction, the solvent was distilled off, and the residue was subjected to desalting by electrodialysis. The thus-desalted product was lyophilized, thereby obtaining 9.5 g (isolation yield: 90%) of 2,6-dimethyl-2,6-dioctyl-4-hydroxy-2,6-diaza-1,7-heptanedicarboxylic acid as white powder.

The $^1$H-NMR data of this product will be shown below.

$^1$H-NMR (D$_2$O): δ(ppm) D$_2$O standard (4.75) 0.82 (triplet,6H,a), 1.22 (broad singlet,20H,b), 1.59 (broad singlet,4H,c), 3.02(singlet,6H,e), 3.05–3.30 (complicated multiplet,8H,d) 3.94 (singlet,4H,f), 4.11 (broad singlet,1H, g).

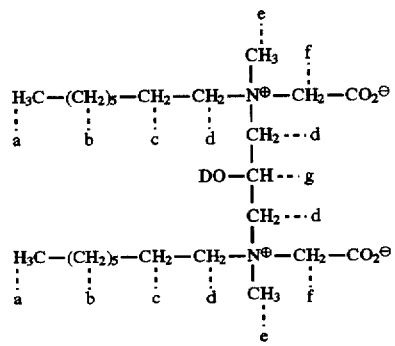

Test Example 4

The foamability of the compound according to Examples 5, 6, 8, 10, 11, 15, 17, 18, 19 and 20, and a comparative compound was tested in accordance with the following method. The results are shown in Table 4.

(Testing method)

A solution obtained by adding 0.1 wt. % of each compound sample and 0.3 wt. % of lanolin to hard water of 40°

C. and 4° DH to dissolve them therein was stirred by a reversal stirring method. Thereafter, the stirring was stopped to measure the volume (ml) of foams generated upon elapsed time of 10 seconds and 120 seconds after the stopping of stirring.

TABLE 4

| Test compound | Volume of foams (ml) | |
|---|---|---|
| | After 10 sec | After 120 sec |
| Compound of Example 5 | 192 | 120 |
| Compound of Example 6 | 180 | 121 |
| Compound of Example 8 | 180 | 93 |
| Compound of Example 10 | 185 | 103 |
| Compound of Example 11 | 190 | 115 |
| Compound of Example 15 | 182 | 105 |
| Compound of Example 17 | 190 | 110 |
| Compound of Example 18 | 195 | 154 |
| Compound of Example 19 | 190 | 115 |
| Compound of Example 20 | 185 | 100 |
| $C_{12}H_{25}O(CH_2CH_2O)_{3.0}SO_3Na$ (Comparative Example) | 170 | 90 |

Table 4 revealed that the compounds according to the present invention have excellent foaming power in a slight amount.

Test Example 5

The irritativeness to the skin was tested in accordance with the following method.
(Testing method)

After the fur of side abdominal regions of guinea pigs (n=5) were sheared off, 30 mg of a 10% solution of a sample was applied thereto in the form of a circle of about 2 cm in diameter (8 times in total). After the solution was applied once a day for 4 days, the condition of the skin applied with the solution was judged and ranked in 5 grades in accordance with the following standard. Each score was calculated as an average value of guinea pigs

TABLE 5

| Ranking of skin condition | |
|---|---|
| No irritation is observed. | 0 |
| Erythema is slightly observed. | 1 |
| Erythema is clearly observed. | 2 |
| Erythema and edema are observed. | 3 |
| Erythema edema and phlycetenae are observed. | 4 |

(Result)

TABLE 6

| Compound | Score |
|---|---|
| Triethanolamine lauryl sulfate | 1.8 |
| Compound of Example 16 | 0.0 |
| Compound of Example 17 | 0.0 |
| Compound of Example 8 | 0.0 |

Table 6 revealed that the compounds according to the present invention are clearly weak in irritativeness to the skin compared with triethanolamine lauryl sulfate.

Formulation Example 1

A shampoo having the following composition was prepared using the compound according to the present invention.

| (Composition) | (wt. %) |
|---|---|
| Compound of Example 1 | 15.0 |
| Lauroyldiethanolamide | 3.0 |
| Lauryldimethylamine oxide | 0.5 |
| Hydroxyethylcellulose (product of Daicel Chemical Industries, Ltd.) | 0.1 |
| Sodium benzoate | 0.3 |
| Coloring matter | Proper amount |
| Perfume base | Proper amount |
| Citric acid | Proper amount |
| Water | Balance |
| Total | 100.0 |

Formulation Example 2

Shampoos were prepared in the same manner as in Formulation Example 1 except that the compounds of Examples 2, 3, 5, 6, 8, 10, 11, 12, 13, 15, 17, 18, 19 and 20 were separately used instead of the compound of Example 1.

All the shampoos obtained in Formulation Examples 1 and 2 were excellent in foamability and detergency, and good even in feel upon shampooing and rinsing.

Formulation Example 3

A body shampoo having the following composition was prepared using the compound according to the present invention.

| (Composition) | (wt. %) |
|---|---|
| Compound of Example 1 | 17.0 |
| Polyoxyethylene (EO 3) laurylglucoside | 5.0 |
| Lauryldimethylamine oxide | 3.0 |
| Glycerin | 4.0 |
| Sucrose fatty acid ester | 1.0 |
| Methylparaben | 0.3 |
| Coloring matter | Proper amount |
| Perfume base | Proper amount |
| Citric acid | Proper amount |
| Water | Balance |
| Total | 100.0 |

Formulation Example 4

Body shampoos were prepared in the same manner as in Formulation Example 3 except that the compounds of Examples 2, 3, 5, 6, 8, 10, 11, 12, 13, 15, 17, 18, 19 and 20 were separately used instead of the compound of Example 1.

All the body shampoos obtained in Formulation Examples 3 and 4 were excellent in foamability and detergency, and good even in feeling after washing because they gave a moisturized feeling.

Formulation Example 5

A face cleanser having the following composition was prepared using the compound according to the present invention.

| (Composition) | (wt. %) |
|---|---|
| Potassium laurate | 4.0 |
| Potassium myristate | 4.0 |

-continued

| (Composition) | (wt. %) |
|---|---|
| Compound of Example 2 | 10.0 |
| Glycerin | 15.0 |
| Ethylene glycol distearate | 2.0 |
| Cationic cellulose | 0.2 |
| Water | Balance |
| Total | 100.0 |

Formulation Example 6

A face cleanser having the following composition was prepared using the compound according to the present invention.

| (Composition) | (wt. %) |
|---|---|
| Compound of Example 2 | 8.0 |
| Potassium monolauryl phosphate | 6.0 |
| Potassium laurate | 2.0 |
| Potassium myristate | 2.0 |
| Potassium stearate | 2.0 |
| Stearic acid | 4.0 |
| Octylglycoside | 3.0 |
| 1,3-Butylene glycol | 10.0 |
| Perfume base | Trace amount |
| Water | Balance |
| Total | 100.0 |

Both face cleansers obtained in Formulation Examples 5 and 6 were excellent in foamability and detergency, and good even in feeling after face washing because they gave a moisturized feeling.

Test Example 6

Dishwashing detergents having their corresponding compositions shown in Table 7 were prepared to evaluate them in foaming power, detergency and feel upon use (feeling of touch to the hands).
(Testing methods)
(1) Test of foaming power:

A commercially-available butter was added in an amount of 1.0 wt. % as a smear component to a 1.0 wt. % aqueous solution of each detergent sample (hardness of water used: 3.5° DH at 40° C.) to determine the foaming power at this time. The determination was conducted in the following manner. A glass cylinder having a diameter of 5 cm and a height of 12 cm was charged with 40 ml of the detergent solution with the butter added thereto. The solution was rotationally stirred for 10 minutes to measure the height of foams generated right after stopping the stirring. In this test, the height of the foams is preferably 80 mm or higher.
(2) Test of feel upon use One liter of a 5.0 wt. % aqueous solution of each detergent sample (hardness of water used: 3.5° DH at 40° C.) was placed in 2-liter beakers to immerse hands to their wrists therein. Upon elapsed time of 5 minutes after the immersion, the hands were thoroughly rinsed with running water of 40° C. and dried with a dry towel to score the feel upon use in accordance with the following evaluation standard:

Good: +2
Somewhat good: +1
Toss-up: 0
Somewhat poor: −1
Poor: −2

The above-described test was conducted on ten panelists, and the feel upon use of the detergent sample was evaluated by the sum total of scores obtained. In this test, the total score is desirably 10 points or higher.
(3) Test of detergency Beef tallow with 0.1 wt. % of Sudan III (a red coloring matter) added thereto was applied in an amount of 2.5 g to a porcelain dish (diameter: 25 cm). The thus-coated dish was rubbed and washed at 40° C. by means of a sponge with 3 g of a detergent sample and 27 g of water (hardness: 3.5° DH) soaked therein. The detergency was evaluated by the number of dishes cleansed until the beef tallow had become free from clean removal.
(Results)

As a result, as shown in Table 7, it is revealed that the dishwashing detergents in which the compounds according to the present invention are separately incorporated are good in foaming power, high in detergency and free of irritation to the hands and give users a pleasant feel upon use.

TABLE 7

| | (wt. %) Invention product | | |
|---|---|---|---|
| Component | 1 | 2 | 3 |
| Compound of Example 12 | 15 | — | — |
| Compound of Example 18 | — | 10 | — |
| Compound of Example 10 | — | — | 10 |
| Dodecyldimethylamine oxide | 3 | — | — |
| Laurylmonoethanolamide | — | 5 | — |
| Polyoxyethylene (EO 8) dodecyl ether | 2 | 5 | 10 |
| Ethanol | 3 | 3 | 3 |
| Na m-xylenesulfonate | 2 | 2 | 2 |
| $MgSO_4 \cdot 7H_2O$ | — | 2 | — |
| Water | Balance | Balance | Balance |
| Foaming power (mm) | 88 | 85 | 90 |
| Feel upon use | 12 | 12 | 12 |
| Detergency | 12 | 13 | 12 |

Formulation Example 7

A powdery laundry detergent composition having the following composition was prepared. This detergent composition was excellent in detergency at a low temperature (5° C.), and its detergency was not impaired even when water high in hardness (4–8° DH) was used.

| (Composition) | (wt. %) |
|---|---|
| Compound of Example 2, 4 or 8 | 5.0 |
| Polyoxyethylene (EO 4–18) $C_6-C_{22}$-alkyl ether | 3.0 |
| Na $C_{12}$-alkylbenzenesulfonate | 20.0 |
| Na $C_{12}-C_{14}$-alkylsulfate | 5.0 |
| Na salt of $C_{12}-C_{18}$ fatty acid | 6.0 |
| Zeolite (4A type) | 30.0 |
| Sodium carbonate | 20.0 |
| Enzyme (protease, cellulase) | 2.0 |
| Polymer (acrylic acid-maleic acid copolymer, Mw = 50,000) | 3.0 |
| Fluorescent dye (DM type, Tinopal CBS mixed system) | 0.5 |
| Perfume base | 0.2 |
| Water | Balance |
| Total | 100.0 |

Formulation Example 8

A powdery laundry detergent composition having the following composition was prepared. This detergent composition was excellent in an effect of finishing washed clothes softly and with good hand and feel.

| (Composition) | (wt. %) |
|---|---|
| Compound of Example 2, 4 or 8 | 10.0 |
| Polyoxyethylene (EO 4–18) $C_6$–$C_{22}$-alkyl ether | 25.0 |
| Cationic cellulose | 3.0 |
| Na salt of $C_{12}$–$C_{18}$ fatty acid | 6.0 |
| Zeolite (4A type) | 20.0 |
| Sodium carbonate | 20.0 |
| Amorphous aluminosilicate ($Na_2O.Al_2O_3.3SiO_2$) | 10.0 |
| Enzyme (protease, cellulase) | 2.0 |
| Polymer (acrylic acid-maleic acid copolymer, Mw = 50,000) | 3.0 |
| Fluorescent dye (DM type, Tinopal CBS mixed system) | 0.5 |
| Perfume base | 0.2 |
| Water | Balance |
| Total | 100.0 |

Formulation Example 9

A powdery laundry detergent having the following composition and composed principally of a nonionic surfactant was prepared. According to this detergent, the disadvantages that foaming upon washing is little and rinsability is poor, which are problems involved in the conventional detergents composed principally of a nonionic surfactant, were improved.

| (Composition) | (wt. %) |
|---|---|
| Compound of Example 2, 4 or 8 | 5.0 |
| Polyoxyethylene (EO 4–18) $C_6$–$C_{22}$-alkyl ether | 22.0 |
| Na salt of $C_{12}$–$C_{18}$ fatty acid | 1.0 |
| Zeolite (4A type) | 30.0 |
| Sodium carbonate | 23.0 |
| Amorphous aluminosilicate ($Na_2O.Al_2O_3.3SiO_2$) | 10.0 |
| Enzyme (protease, cellulase) | 2.0 |
| Polymer (acrylic acid-maleic acid copolymer, Mw = 100,000) | 3.0 |
| Fluorescent dye (DM type, Tinopal CBS mixed system) | 0.5 |
| Perfume base | 0.2 |
| Water | Balance |
| Total | 100.0 |

Test Example 7

Liquid detergent compositions having their corresponding compositions shown in Table 8 were prepared to evaluate them in detergency.

(Testing method)
(1) Dirty cloth smeared with sebum (artificial dirty cloth)

| <Composition of model sebum smear> | (wt. %) |
|---|---|
| Cottonseed oil | 60 |
| Cholesterol | 10 |
| Oleinic acid | 10 |
| Palmitic acid | 10 |
| Liquid and solid paraffins | 10 |

The model sebum smear having the above-described composition is evenly coated on a cotton cloth having a size of 10 cm×10 cm.

(2) Dirty cloth stained with mud (artificial dirty cloth)

Kanuma red-ball soil for gardening was dried for 4 hours at 120° C.±5° C. and then ground. The −150 mesh powder (100 μm) of the ground soil was dried for 2 hours at 120° C.±5° C. and then dispersed in an amount of ±150 g in 1,000 ml of perclene. A shirting #2023 was brought into contact with the thus-obtained dispersion and brushed to remove the dispersion, thereby eliminating stain adhered in excess (see Japanese Patent Application Laid-Open No. 26473/1980).

(3) Washing conditions and evaluating method

Each five dirty cloths stained with mud and smeared with sebum (artificial dirty cloths) having a size of 10 cm×10 cm were immersed in 1 liter of an aqueous solution of a detergent sample for evaluation and washed by a Turgot meter at 100 rpm under the following conditions. The washing conditions are as follows:

| <Washing conditions> | |
|---|---|
| Washing time | 10 minutes |
| Washing concentration | 0.0133 wt. % |
| Hardness of water | 4° DH |
| Temperature of water | 20° C. |
| Rinsing | 5 minutes with tap water. |

The detergency was evaluated by measuring reflectances of the raw cloths before staining or smearing and the dirty cloths before and after washing at 460 nm by an autocolorimeter (Z-300A, manufactured by Nippon Denshoku K.K.) and determining a cleaning rate (%) in accordance with the following equation (in the table, indicated by an average value of 5 cloths):

$$\text{Cleaning rate (\%)} = \frac{\text{Reflectance after washing} - \text{Reflectance before washing}}{\text{Reflectance or raw cloth} - \text{Reflectance before washing}}$$

(Results)

As a result, as shown in Table 8, the detergents in which the compounds according to the present invention were separately incorporated were excellent in detergency to sebum smear and mud stain.

TABLE 8

| | Invention product | | | | | | | Comparative product | | |
|---|---|---|---|---|---|---|---|---|---|---|
| Component (wt. %) | 4 | 5 | 6 | 7 | 8 | 9 | 10 | 11 | 1 | 2 | 3 |
| Compound of Example 12 | 40 | | | | 20 | | | | | | |
| Compound of Example 18 | | 40 | | | | 35 | | | | | |
| Compound of Example 11 | | | 40 | | | | 35 | | | | |
| Compound of Example 6 | | | | 40 | | | | 35 | | | |

TABLE 8-continued

| Component (wt. %) | Invention product | | | | | | | | Comparative product | | |
|---|---|---|---|---|---|---|---|---|---|---|---|
| | 4 | 5 | 6 | 7 | 8 | 9 | 10 | 11 | 1 | 2 | 3 |
| Polyoxyethylene (EO 7) alkyl ($C_{12}$-$C_{15}$) ether | | | | | 20 | 5 | | | 40 | | |
| Sodium linear dodecyl-benzenesulfonate | | | | | | | 5 | | | 40 | |
| Sodium polyoxyethylene (EO 2.5) alkyl ($C_{12}$-$C_{15}$) ether sulfate | | | | | | | | 5 | | | 40 |
| Monoethanolamine | 2 | 2 | 2 | 2 | 2 | 2 | 2 | 2 | 2 | 2 | 2 |
| Enzyme (protease, etc.) | | | | | Proper amount | | | | | | |
| Water and other miner components | B* | B* | B* | B* | B* | B* | B* | B* | B* | B* | B* |
| Evaluation: | | | | | | | | | | | |
| Detergency to sebum smear (%) | 63 | 67 | 66 | 64 | 70 | 68 | 69 | 67 | 58 | 45 | 55 |
| Detergency to mud stain (%) | 40 | 41 | 44 | 43 | 44 | 45 | 46 | 43 | 35 | 36 | 35 |

Note)
B*: Balance of 100 in total.

Test example 8

Liquid detergent compositions having their corresponding compositions shown in Table 9 were prepared to evaluate them in softness-imparting ability to various kinds of fibers.

(1) Treating method and washing conditions

Commercially-available cotton towel and acrylic jersey were repeatedly washed 5 times with a commercially-available detergent "Attack" (product of Kao Corporation, trade mark) to remove textile auxiliaries adhered to each clothing. Thereafter, the clothes were washed for 10 minutes with a 0.04 wt. % aqueous solution (hard water of 2° DH) of each of the detergent compositions having their corresponding formulations shown in Table 2 at 20° C. and a bath ratio of 1/30 in a household two-tub washing machine (swirl type), dried for 1 minute and then rinsed out for 5 minutes in standing tap water.

(2) Evaluating method

The clothes treated in the above-described manner were air-dried in a room and then left over for 24 hours in an air-conditioned room of 25° C. and 65% RH. These clothes were evaluated in softness-imparting ability. Softness-imparting ability: Those obtained by washing the same clothes as described above with the commercially-available detergent "Attack" under the above-described conditions were used as controls to make paired comparison in accordance with the following standard:

+3: Very soft
+2: Soft
+1: Somewhat soft
0: Comparable with the control
−1: Somewhat hard
−2: Hard
−3: Very hard.

(Results)

As apparent from Table 9, it was revealed that the detergents compositions according to the present invention have sufficient softness-imparting ability for the cotton and acrylic compared with the commonly-used detergents.

TABLE 9

| Component (wt. %) | Invention product | | | Comparative product | | |
|---|---|---|---|---|---|---|
| | 12 | 13 | 14 | 4 | 5 | 6 |
| Compound of Example 18 | 40 | | | | | |
| Compound of Example 11 | | 40 | | | | |
| Compound of Example 6 | | | 40 | | | |
| Polyoxyethylene (EO 7) alkyl ($C_{12}$-$C_{14}$) ether | | | | 40 | | |
| Sodium linear dodecyl-benzenesulfonate | | | | | 40 | |
| Sodium polyoxyethylene (EO 2.5) alkyl ($C_{12}$-$C_{14}$) ether sulfate | | | 12 | | | 40 |
| Monoethanolamine | 2 | 2 | 2 | 2 | 2 | 2 |
| Water, enzyme and others | B* | B* | B* | B* | B* | B* |
| Evaluation of softness-imparting ability: | | | | | | |
| Cotton towel | +2 | +2 | +2 | 0 | 0 | 0 |
| Acrylic jersey | +3 | +2 | +2 | 0 | −1 | 0 |

Note) B*: Balance of 100 in total.

INDUSTRIAL APPLICABILITY

2-Hydroxypropanediamine derivatives, or salts or quaternized products thereof, which are novel compounds according to the present invention, are excellent in foamability and low in irritativeness to the skin and the like, and can give a pleasant feeling to the user's skin, hair and the like. Therefore, the compounds according to the present invention are useful as bases for hair and skin cosmetic compositions, detergents, emulsifying agents, wetting agents, conditioning agents, modifying agents or the like.

We claim:

1. A compound represented by the general formula (1):

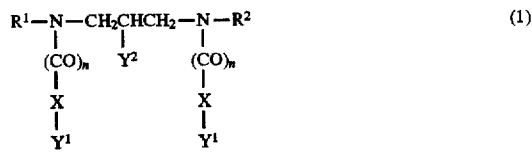

wherein $R^1$ and $R^2$ are identical with or different from each other and mean individually a linear or branched alkyl or alkenyl group having 6–36 carbon atoms, X denotes an alkylene or alkenylene group which may be substituted by at least one hydroxyl, sulfonic or carboxyl group and has 1–6 carbon atoms, $Y^1$ is a sulfonic group, a sulfuric acid residue or a carboxyl group, $y^2$ means a hydroxyl group, a sulfuric acid residue or

—OCX—COOH, and n stands for 0 or 1, or a salt or quaternized product thereof, with the proviso that when n stands for zero, $y^2$ is a hydroxyl group and the nitrogen atoms of the formula are not quaternized, then X is not a methylene group.

2. The compound according to claim 1, wherein $y^1$ is a carboxyl group, and $Y^2$ is a hydroxyl group or

—OCX—COOH.

3. The compound according to claim 1, wherein $R^1$ and $R^2$ are individually a linear or branched alkyl or alkenyl group having 6–24 carbon atoms.

4. The compound according to claim 2, wherein $R^1$ and $R^2$ are individually a linear or branched alkyl or alkenyl group having 6–24 carbon atoms.

5. The compound according to claim 1, wherein $R^1$ and $R^2$ are individually a linear or branched alkyl or alkenyl group having 6–18 carbon atoms.

6. The compound according to claim 1, which is in the form of a free base or a salt.

7. The compound according to claim 2, which is in the form of a free base or a salt.

8. The compound according to claim 7, which is in the form of a free base or a salt.

9. A detergent composition comprising the compound according to claim 1 and a surfactant.

10. A compound represented by the general formula (1):

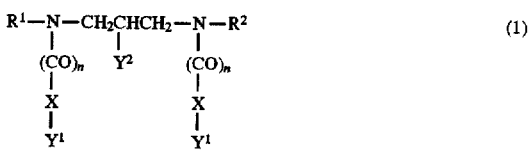

wherein $R^1$ and $R^2$ are identical with or different from each other and mean individually a linear or branched alkyl or alkenyl group having 6–36 carbon atoms, X denotes an alkylene or alkenylene group which may be substituted by at least one hydroxyl, sulfonic or carboxyl group and has 1–6 carbon atoms, $Y^1$ is a sulfonic group or a sulfuric acid residue, $y^2$ means a hydroxyl group or a sulfuric acid residue or

—OCX—COOH, and n stands for 0 or 1, or a salt or quaternized product thereof.

11. The compound according to claim 10, wherein $R^1$ and $R^2$ are individually a linear or branched alkyl or alkenyl group having 6–24 carbon atoms.

12. The compound according to claim 10, wherein $R^1$ and $R^2$ are individually a linear or branched alkyl or alkenyl group having 6–18 carbons.

13. The compound according to claim 10, which is in the form of a free base or a salt.

14. A detergent composition comprising the compound according to claim 10, and a surfactant.

15. A detergent composition according to claim 14, wherein $R^1$ and $R^2$ are individually a linear or branched alkyl or alkenyl group having 6–18 carbons.

* * * * *